US005932481A

United States Patent [19]
Pon et al.

[11] Patent Number: 5,932,481
[45] Date of Patent: Aug. 3, 1999

[54] METHOD FOR MEASURING METAPLASTIC CHANGES OF MUCUS SECRETING EPITHELIAL CELLS

[75] Inventors: Douglas J. Pon; Louise Boulet; Carlo J. van Staden; Rejean Fortin, all of Quebec, Canada

[73] Assignee: Merck Frosst Canada & Co., Kirkland, Canada

[21] Appl. No.: 09/046,085

[22] Filed: Mar. 23, 1998

Related U.S. Application Data

[63] Continuation of application No. 08/605,098, filed as application No. PCT/CA94/00473, Aug. 30, 1994, abandoned, which is a continuation-in-part of application No. 08/120,719, Sep. 13, 1993, abandoned.

[51] Int. Cl.$^6$ .................................................. G01N 33/48
[52] U.S. Cl. .............................. 436/87; 436/86; 436/63; 436/161; 436/164; 436/166; 436/174; 436/175; 436/177
[58] Field of Search ................................ 436/86, 87, 63, 436/161, 164, 166, 174, 175, 177

[56] References Cited

U.S. PATENT DOCUMENTS

| | | | |
|---|---|---|---|
| 4,078,082 | 3/1978 | Lakah | 514/574 |
| 5,015,631 | 5/1991 | Ogasawara | 514/53 |

OTHER PUBLICATIONS

M. C. Rose, *Am. Physiol. Soc.*, 263, pp. L413–L429, (1992).
G. Lamblin et al., *Eur. Respir. J.*, 5, pp. 247–256 (1992).
M. C. Rose, *Horm. metabol. Res.*, 20, pp. 601–608, (1988).
L. Reid et al., *Thorax*, 15, pp. 132–141 (1960).
T. Aikawa, *Chest*, 101, pp. 916–921 (1992).
J. Stolk, *J. of Pathology*, 167, pp. 349–356 (1992).
J. R. Harkema et al., *Am. J. of Pathology*, 141, No. 2, pp. 307–317 (Aug. 1992).
D. Lamb et al., *J. Path. Bact.*, 96, pp. 97–111 (1968).
B. Jany et al., *Biochem. & Biophys. Res. Comm.*, 181, No. 1, pp. 1–8, (1991).
J. O. Lotval et al., *Am. Rev. Respir. Dis.*, 142, pp. 1390–1395 (1990).
M. V. Pino et al., *Am. Rev. Respir. Dis.*, 145, pp. 882–889 (1992).
J. M Farley, *Annu. Rev. Pharmacol. Toxicol.*, 32, pp. 67–88 (1992).
D. J. Steiger, Abstract, *Am. Rev. Resp. Dis.*, 147, p. A437 (1993).
J. E. Scott et al., *Histochemie*, 5, pp. 221–233 (1965).
U. K. Laemmli, *Nature*, 227, pp. 680–685 (1970).
H. Towbin et al. *Proc. Natl. Acad. Sci. USA*, 76, No. 9, pp. 4350–4354 (Sep. 1979).
A. N. Douglas, *Thorax*, 35, pp. 198–201 (1980).
P.–W. Cheng et al., *J. Clin. Invst.*, 84, pp. 68–72 (1989).
R. C. Frates et al., *Pediatr. Res.*, 17, pp. 30–34 (1983).
T. P. Mawhinney et al., *Carb. Res*, 235, pp. 179–197 (1992).
M. Mantle et al., *Biochem. Soc. Trans.*, 6, pp. 607–609 (1978).
D. J. Thornton, *Anal. Biochem.*, 182, pp. 160–164 (1989).
R. L. Hall et al.,Abstract, *Biochem. Soc. Trans.*, 8, 72 (1980).
T. Kaizu et al., *Comp. Biochem. Physiol.*, 62B, pp. 195–200 (1978).
J. Sturgess et al., *Br. J. exp. Path.*, 54, pp. 388–403 (1973).
W. S. Tyler, et al., *Fund. Appl. Toxic.*, 5, pp. 405–422 (1985).
W. E. Finkbeiner et al., *Am. J. Path.*, 131, pp. 290–297 (1988).
J. M. Fine et al., *Am. Rev. Respir. Dis.*, 136, pp. 1112–1126 (1987).
Harris et al. "Protein Purification Methods–A Practical Approach", pp. 57–65, 87–91, 94–97 (1989).
Dimitriadis et al.,Experimental Lung Research vol. 18, pp. 731–742 (1992).
Harkema et al., Toxicology Letters, vol. 68, pp. 251–263 (Jun. 16, 1993).
Pon et al., American Journal of Respiratory Cell and Molecular Biology, vol. 10 No. 6, pp. 625–634 ISSN: 1044–1549 (1994).
Harkema et al., Journal of Histochemistry and Cytochemistry, New York, US, vol. 35, No. 3, pp. 279–286 (1987).
Jones, R. et al., Histochem., J. , vol. 5, pp. 9–18, (1973).
Tooi Nippon Geka Gakkai Zasshi, K., vol. 78, pp. 327–344, (1977.).

(List continued on next page.)

*Primary Examiner*—Arlen Soderquist
*Attorney, Agent, or Firm*—J. Mark Hand; Joanne M. Giesser; Jack L. Tribble

[57] ABSTRACT

A method for the rapid estimation of hyperplastic and hypertrophic changes in animal airways is an assay which specifically measures acidic and neutral mucoproteins in a linear fashion from 0.5 to at least 10 μg. The assay comprises exposure of a test animal to a suspected metaplastic inducer, removal of the lungs, homogenization in an appropriately buffered solution containing reducing agents and protease inhibitors; removal of particulate matter; and size-fractionation of the SDS treated soluble extract. The high molecular weight material is immobilized and stained for either acidic or neutral mucosubstances and the specific staining is quantitated. The changes observed are consistent with those seen in histological sections of the exposed tissues. The assay is useful in confirming the metaplastic potential of suspected compounds, in determining what neurohumoral mediator(s) are involved in mucus cell metaplasia in animal models for chronic obstructive pulmonary disease, and in identifying compounds which might ameliorate these effects.

20 Claims, 13 Drawing Sheets

OTHER PUBLICATIONS

Carlstedt, I., et al., Biochem. J., vol. 211, pp. 13–22, (1983.).
Wilson, T.S. et al., Stain Technology, vol. 58, pp. 225–229 (1983).
Stanley, R.A. et al., Biochem. Biophys. Acta, vol. 760, pp. 262–2699 (1983).
Cogburn, J. et al., J. Phycol., vol. 20, pp. 533–544, (1984).
Buk, S. J. et al., Histochem. J., vol. 18, pp. 576–578, (1986).
Munakata, H., et al. J. Biochem., vol. 19, pp. 503–507, (1987).
Gearhart, J. M., et al. Exp. Lung Res., vol. 14, pp. 587–605, (1988).
Okamura, T. et al., J. Jpn. Med. Soc. Biol. Interface, vol. 21, pp. 19–35, (1990).
Jay, G. D., et al. Anal. Biochem, vol. 185, pp. 324–330, (1990).
Rudolphus, A., et al., Eur. Respir. J., vol. 4, pp. 31–39, (1991).
Lee, S. P., et al., Biochem. Cell Biol., vol. 69, pp. 566–571, (1991).

METHOD FOR MEASURING METAPLASTIC CHANGES OF MUCUS SECRETING EPITHELIAL CELLS

This is a continuation application of application Ser. No. 08/605,098, filed Mar. 1, 1996, now abandoned, which was a National Stage application of PCT/CA94/00473, filed Aug. 30, 1994, which is a continuation-in-part of application Ser. No. 08/120,719, filed Sep. 13, 1993, now abandoned.

BACKGROUND OF THE INVENTION

Mucus glycoproteins are the major constituents of the mucosal layer found in the upper and lower airways of mammalian lungs [Rose. M. C. (1992), Am. J. Physiol. 263:L413-LA29]. Mucus confers the viscoelastic properties upon airway secretions and thus provides for the lubricative and protective qualities necessary for optimal mucocilliary clearance of foreign material from the lungs [Lamblin, G., et al. (1992) Eur. Resp. J. 5:247–256]. In certain disease states such as cystic fibrosis [Rose, M. C. (1988) Horm. metabol. Res. 20:601–609], acute and chronic bronchitis [Reid, L. (1960) Thorax 15:132–141], and asthma [Aikawa, T., S. Shimura, (1992) Chest 101:916–921], a situation exists where there is a hypersecretion of mucus glycoproteins from the airway secretory cells of afflicted patients. Hypersecretion of mucus glycoprotein into the luminal airway space may result in obstruction of bronchiolar passages and provide a milieu for bacterial colonization [Rose, M. C. (1992) Am. J. Physiol. 263:L413–L429]. Thus, an excess presence of mucus may lead to impaired mucocilliary clearance, progressive respiratory insufficiency, and may ultimately contribute to the morbidity and mortality associated with the above mentioned diseases.

The underlying neural and cellular mechanisms which contribute to the metaplastic changes of the airway epithelial cells that lead to mucus hypersecretion are not well understood. In order to study these mechanisms, investigators have subjected small animals to irritants such as endotoxin [Stolk, J., A. (1992) J. Pathol. 167:349–356; Harkema, J. R. and J. A. Hotchkiss. (1992) Am. J. Pathol. 141:307–317], $SO_2$ [Lamb, D. and L. Reid. (1968) J. Path. Bact. 96:97–111; Jany. B., (1991) Biochem. Biophys. Res. Comm. 181:1–8], ozone [Pino, M. V., et al. (1992) Am. Rev. Respir. Dis. 145:882–889], and cigarette smoke [Farley, J. M. (1992) Annu. Rev. Pharmacol. Toxicol. 32:67–88]. Histological studies reveal that endotoxin or $SO_2$ exposure causes a profound increase in the number of mucus containing cells which line both the upper and lower airways of the lung [Stolk, J., et al. (1992) J. Pathol. 167:349–356; Harkema, J. R. and J. A. Hotchkiss (1992) Am. J. Pathol. 141:307–317; Lamb, D. and L. Reid (1968) J. Path. Bact. 96:97–111]. The increase in airway mucus is demonstrated by an increase in number of Alcian blue/Periodic Acid Schiff s (PAS) staining of airway epithelial cells, and by an elevation in $^{35}SO_4$ uptake into explanted airways.

Tracheal lavage samples from endotoxin treated rats also show an increased presence of mucin material as deduced by immunoreactivity with specific monoclonal antibodies [Steiger, D. J., et al. (1993) Am. Rev. Resp. Dis. 147:A437 (abstr.)]. Aside from examining increases in the amounts of mucus glycoprotein through the use of histological and immunological techniques, Basbaum and coworkers, [(1991), Biochem. Biophys. Res. Comm. 181:1–8] have also shown that substantial increases in mRNA coding for mucin are associated with mucus cell metaplasia. Their data suggests that exposing rats to endotoxin [Steiger, D. J., et al. (1993) Am. Rev. Resp. Dis. 147:A437 (abstr.)] or $SO_2$ [Jany, B., (1991). Biochem. Biophys. Res. Comm. 181:1–8] initiates mucin gene transcription resulting in the de novo synthesis of mucus glycoprotein by the airway epithelia cell.

Animal Models of Mucus Hypersecretion

Hypersecretion of mucus glycoproteins by secretory airway epithelial cells in patients afflicted with cystic fibrosis [Rose, M. C. (1988) Horm. metabol. Res. 20:601–608], asthma [Aikawa, T., (1992) Chest 101:916–921], and chronic bronchitis [Reid, L. (1960) Thorax 15:132–141] is thought to contribute to the morbidity and mortality associated with those disease states [Rose, M. C. (1992) Am. J. Physiol. 263:L413–L429]. Histological sections prepared from airway tissue removed from subjects afflicted with airway disease at time of autopsy exhibit mucus plugging of distal airways, increased numbers of mucus containing goblet cells [Aikawa, T., et al. (1992) Chest 101:916–921], and an enlargement of submucosal glands [Douglas, A. N. (1990) Thorax 35:198–201].

The basis for airway obstruction with mucus is unclear, but the concepts of hypersecretion and reduced mucocilliary clearance are two viable explanations. An increase in the number of cells capable of synthesizing and secreting mucus glycoproteins may certainly contribute to the observed mucus plugging of airway passages. Biochemical studies on mucus glycoprotein from individuals with airway disease have demonstrated alterations in sialylation and sulfation of the oligosaccharide chains attached to the mucin protein core [Cheng. P., et al. (1989) J. Clin. invest. 84:68–72; Frates, R. C., et al. (1983) Pediatr. Res. 17:30–34; Mawhinney, T. P., et al. (1992). Carb. Res. 235:179–197]. Changes in the physicochemical nature of mucus in the disease state might impede its removal from the airways by mucocilliary clearance mechanisms, thereby allowing a buildup of material in the airways and eventual plugging.

Numerous laboratories have vigorously pursued the mechanisms underlying the metaplastic changes seen in the secretory airway cells and changes in the physicochemical make-up of secreted mucins. Small animals have been exposed to environmentally relevant irritants that are believed to be causal components in the development of airway disease in man. Models that have been and are still currently used for the study of chronic obstructive pulmonary disease are exposure of animals to $SO_2$ [Lamb, D. and L. Reid. (1968). J. Path. Bact. 96:97–111; Jany. B., et al. (1991). Biochem. Biophys. Res. Comm. 181:1–8], ozone [Pino, M. V., et al. (1992). Am. Rev. Respir. Dis. 145:882–889], cigarette smoke [Farley, J. M. (1992). Annu. Rev. Pharmacol. Toxicol. 32:67–88] and endotoxin [Stolk, J., (1992). J. Pathol. 167:349–356; Harkema, J. R. and J. A. Hotchkiss. (1992). Am. J. Pathol. 141:307–317]. Histological studies performed on these models all demonstrate hypertrophic and hyperplastic changes in the mucus secreting cells lining the airways and, as well, in the submucosal layers of the upper airways. Such changes are comparable to those seen in the above mentioned airway diseases. The neurogenic and humoral mediators responsible for hypersecretion have not been identified todate.

Techniques for Investigating Airway Mucus Cell Metaplasia

Investigators have relied heavily on histological methods for examining changes in airway tissue following irritant exposure [Harkema. J. R. and J. A. Hotchkiss. (1992). Am. J. Pathol. 141:307–317]. Their studies have given detailed accounts of changes in alveolar airspace, airway lumen caliber, basement membrane thickness, cellular infiltration, epithelial sloughing, and size and numbers of mucus containing cells. Use of PAS and Alcian blue staining has allowed for quantitative examinations into the up-regulation of acidic and neutral mucus glycoproteins at different levels in the airway [Lamb, D. and L. Reid. (1968), J. Path. Bact. 96:97–111].

Histological methods, although yielding exquisite detail of changes occurring in the airways, are extremely tedious, time consuming and require a high level of expertise for documenting consistent and reproducible results.

In conjunction with histological methods, investigators have injected radioactive sulphate into animals to examine levels of sulphomucins in the airway cells following $SO_2$ exposure [Lamb, D. and L. Reid. (1968). J. Path. Bact. 96:97–111]. More recently Basbaum and coworkers have used monoclonal antibodies that specifically recognize rat goblet and submucosal cell secretory products [Finkbeiner, W. E. and C. B. Basbaum. (1988). Am. J. Path. 131:290–297].

Tracheal lavage samples from rats given intratracheal instillations of endotoxin show an elevated release of macromolecules into the airway space compared to control. Such studies have extended into transcriptional aspects of mucin gene expression through the use of specific cDNA probes which recognize mRNA coding for mucus glycoprotein. Elevations in mucin mRNA were observed in trachea from animals treated with endotoxin [Steiger, D. J., (1993) Am. Rev. Resp. Dis. 147:A437 (abstr.)], and sendei virus infected rats exposed to $SO_2$ [Jany, B., (1991). Biochem. Biophys. Res. Comm. 181:1–8].

The use of specific antibodies and cDNA probes are particularly useful for examining the up-regulated expression and hypersecretion of specific forms of mucus glycoprotein. However, potential drawbacks for the use of specific antibodies and cDNA probes in exploring various models of hypersecretion are that the available probes may be species, and/or model specific. In addition, the availability of such probes may be limited, especially for investigators unable to develop their own antibodies or cDNA. Such limitations may ultimately hinder the advancement of knowledge concerning the mechanisms leading to airway hypersecretion.

Therefore, in order to examine metaplastic changes in airway mucus secretory cells, investigators have relied heavily on the histological methods which are tedious and are at best semiquantitative. As mentioned above, immunological and molecular biological techniques have been employed by some laboratories to study mucus gene expression and hypersecretion. These techniques are based on the availability of specific antibodies or cDNA probes that recognize the type(s) of mucin which is up-regulated for that particular animal species, strain, and irritant model. The instant invention is a method for the rapid estimation of hyperplastic and hypertrophic changes in animal airways, by directly measuring mucins, regardless of the model, strain, or species, as opposed to indirect measurement of mRNA.

SUMMARY OF THE INVENTION

A method for the rapid estimation of hyperplastic and hypertrophic changes in animal airways is an assay which specifically measures acidic and neutral mucoproteins in a linear fashion from 0.5 µg to at least 10 µg. The assay comprises exposure of a test animal to a suspected metaplastic inducer, removal of the lungs, homogenization in an appropriately buffered solution containing reducing agents and protease inhibitors; removal of particulate matter; treatment with SDS and size-fractionation of the soluble extract. The high molecular weight material is immobilized and stained for either acidic or neutral mucosubstances and the specific staining is quantitated. The changes observed are consistent with those seen in histological sections of the exposed tissues. The assay is useful in confirming the metaplastic potential of suspected compounds, in determining what neurohumoral mediator(s) are involved in mucus cell metaplasia in animal models for chronic obstructive pulmonary disease, in identifying compounds which might ameliorate these effects and in the development of therapeutic agents which would alleviate mucus hypersecretion in persons afflicted with chronic obstructive pulmonary disease.

Samples (1 ml) were incubated with either hyaluronidase or chondroitinase AC. The enzyme digests were rechromatographed and amounts of remaining Alcian blue positive material (panel a) and PAS positive material (panel b) in the void volume were determined. Values are means of 3 separate experiments performed in triplicate ±SEM. MBS= sodium metabisulfite.

Figure 6A:
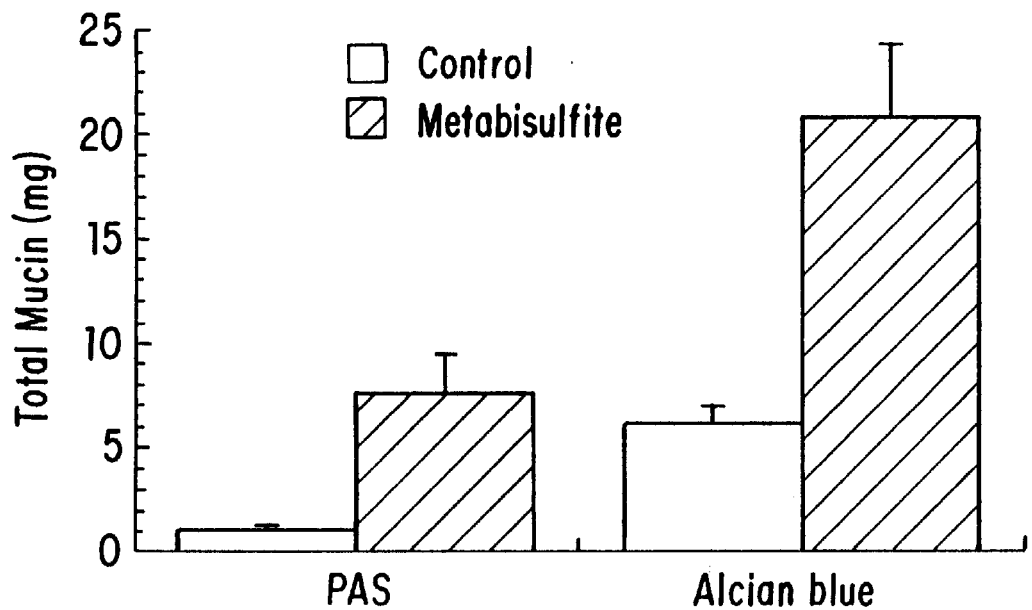
Figure 6B:
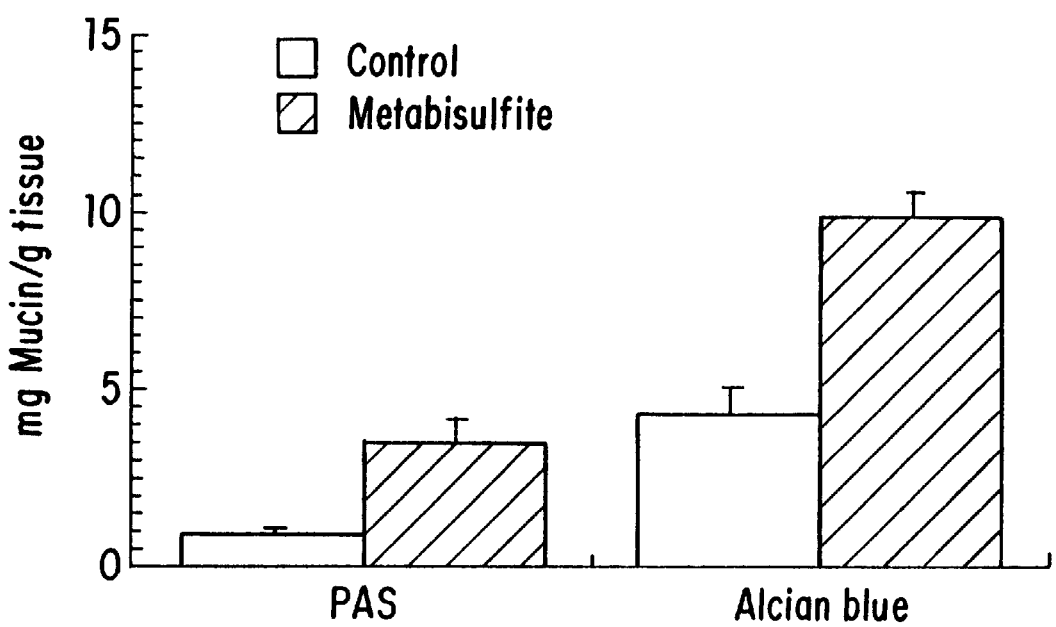

FIG. 6A and 6B. Effect of metabisulfite exposure on rat airway mucin content. Lungs were removed from rats that had been exposed to either $H_2O$ or 10% metabisulfite mist for 3 weeks. Airway mucin content was measured by Sepharose CL-6B chromatography of extracts, deamination of dot-blotted membranes and staining of HMW mucus glycoproteins with either PAS or Alcian blue as described previously. Results are expressed as total whole lung mucins (panel a) or mucins per gram lung tissue (panel b). Control values are means ±SEM of 4 animals; metabisulfite values are means ±SEM of 3 animals. Metabisulfite vs. control $P<0.01$.

Figure 7A:
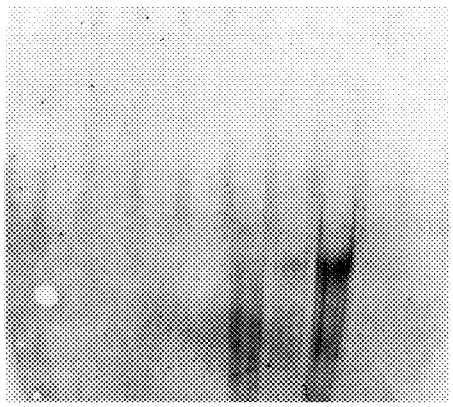
Figure 7B:
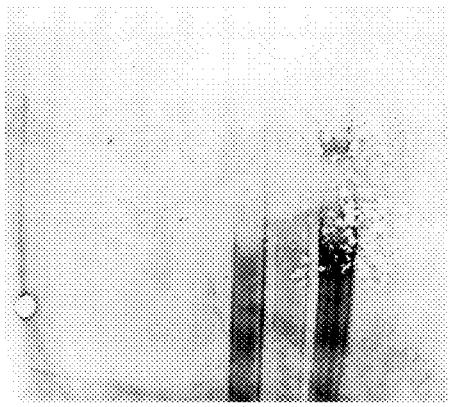

FIG. 7A and 7B. Agarose gel electrophoresis of void volume material from control and metabisulfite exposed rats. Samples obtained from the void volume of Sepharose CL-6B chromatographed airway extracts were incubated in a buffer containing 2% SDS with 10 mM mercaptoethanol at 100° C. for 4 minutes. Samples were loaded onto 2% agarose Tri-glycine gels and electrophoresed at 200 V for 2 h. Proteins were transferred to Immobilon-p™ membranes using a Bio-Rad trans-blot apparatus in a Towbin buffer. Membranes were stained for HMW mucus glycoproteins with PAS (panel a) or Alcian blue (panel b). Lane 1) protein stds.; lanes 2 to 5) control rats; lanes 6–8) metabisulfite exposed rats.

Figure 8A:
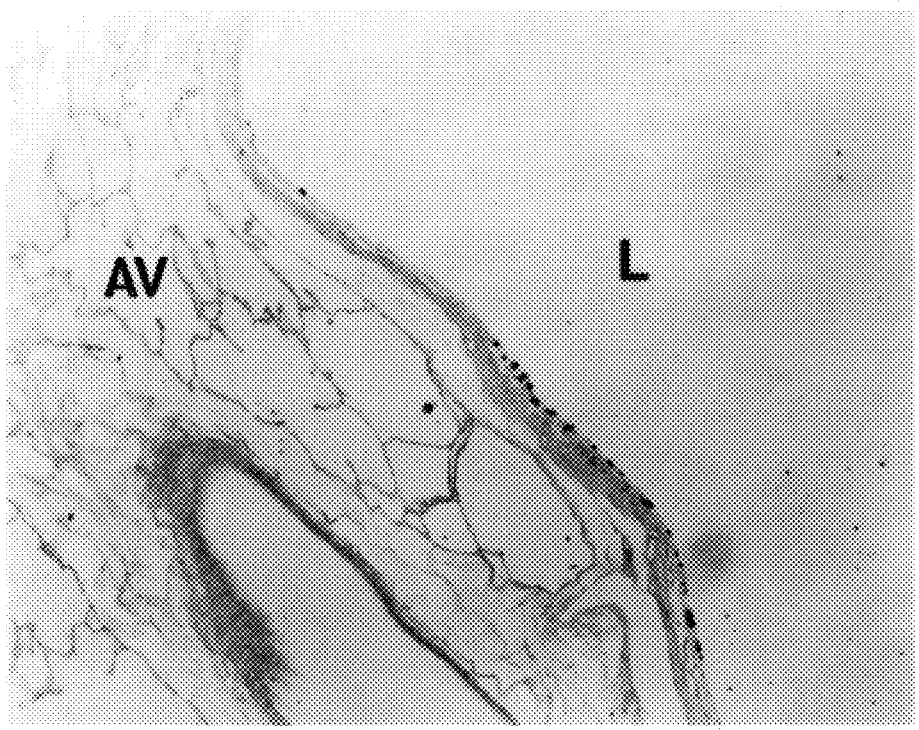
Figure 8A:
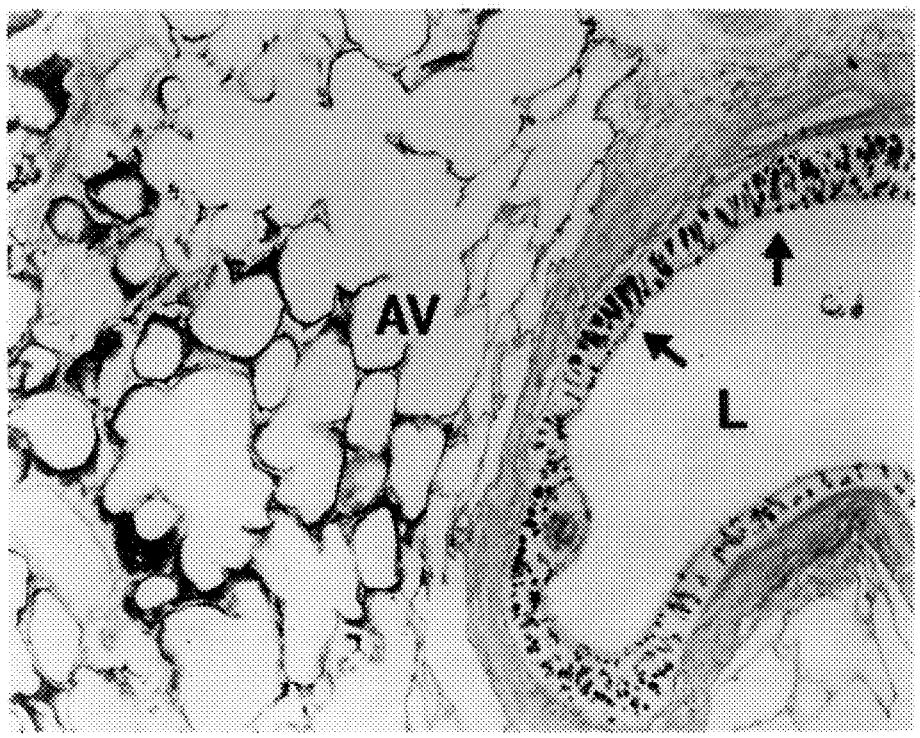

FIGS. 8A and 8B. Combined Alcian blue/PAS staining of lung tissue from rats exposed to aerosolized $H_2O$ or sodium metabisulfite. Tissues from $H_2O$ treated animals (panel (a)) and sodium metabisulfite exposed animals (panel (b)) were fixed and stained with Alcian blue/PAS. Panels (a) and (b) show cross-sectional areas of the left lobe which contains a secondary bronchus. The arrows in panel (b) highlight areas of intense Alcian blue/PAS staining of the epithelial cell layer of sodium metabisulfite treated animals. AV=alveolar space; L=bronchial luminal space.

Figure 9A:
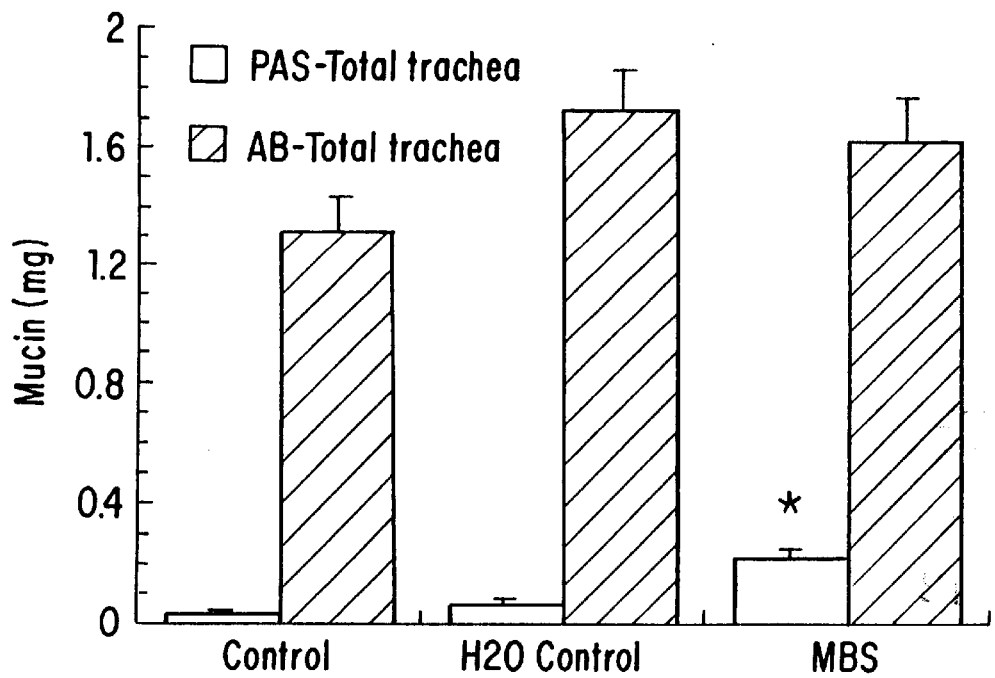
Figure 9B:
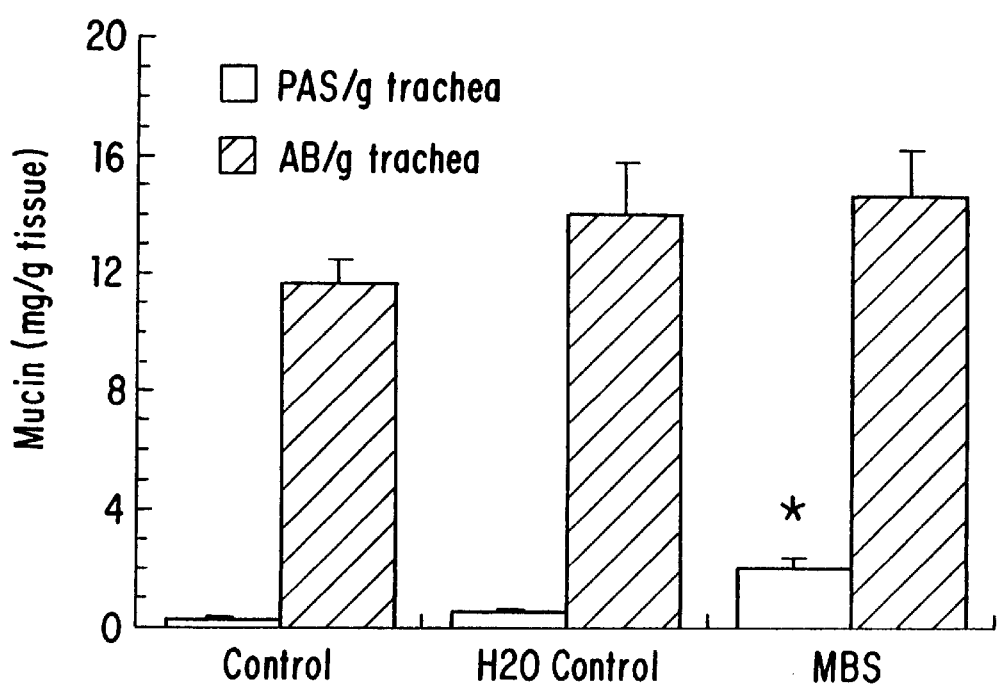

FIGS. 9A and 9B. Effect of sodium metabisulfite exposure on rat tracheal mucin content. Tracheae were removed from rats that had been exposed to either room air, $H_2O$ or 10% sodium metabisulfite mist for 3 weeks. Airway mucin content was measured by Sepharose CL-6B chromatography of extracts, deamination of dot-blotted membranes and staining of HMW mucus glycoproteins with either PAS or Alcian blue as described previously. Results are expressed as total tracheal mucins (panel a) or mucins per gram tracheal tissue (panel b). Control values are means ±SEM of 4 animals; sodium metabisulfite values are means ±SEM of 3 animals. *Sodium metabisulfite vs. $H_2O$ control $P<0.01$.

Figure 10:
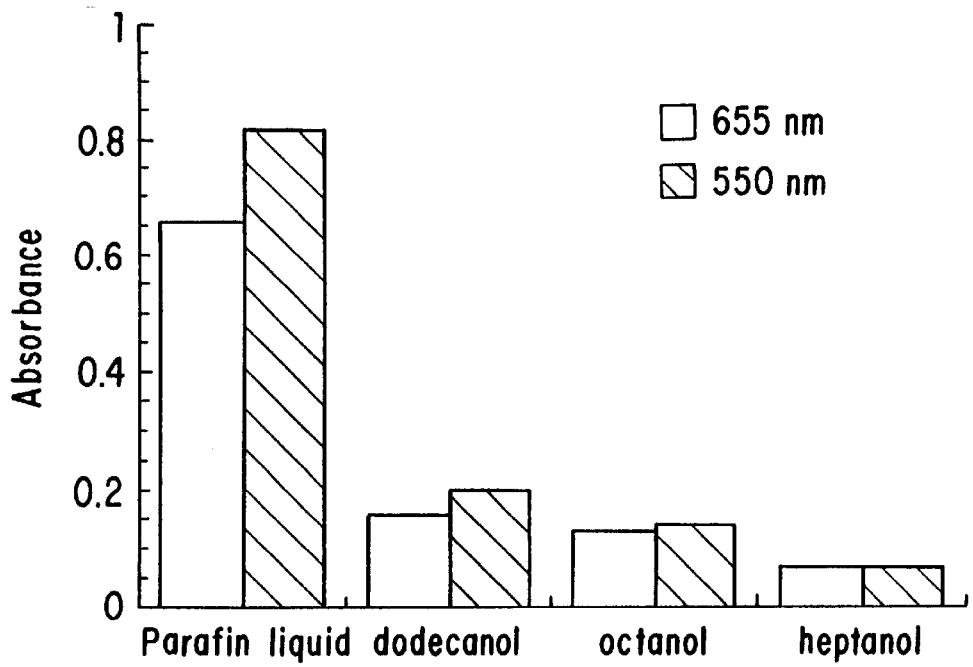

FIG. 10. Effect of organic solvents on Immobilon-P membrane translucence. Immobilon-p™ membranes were immersed in the indicated solutions and placed face-down on the bottom of a 96 well flat bottom ELISA plate and the background optical density measured at the indicated wavelengths.

Figure 11:
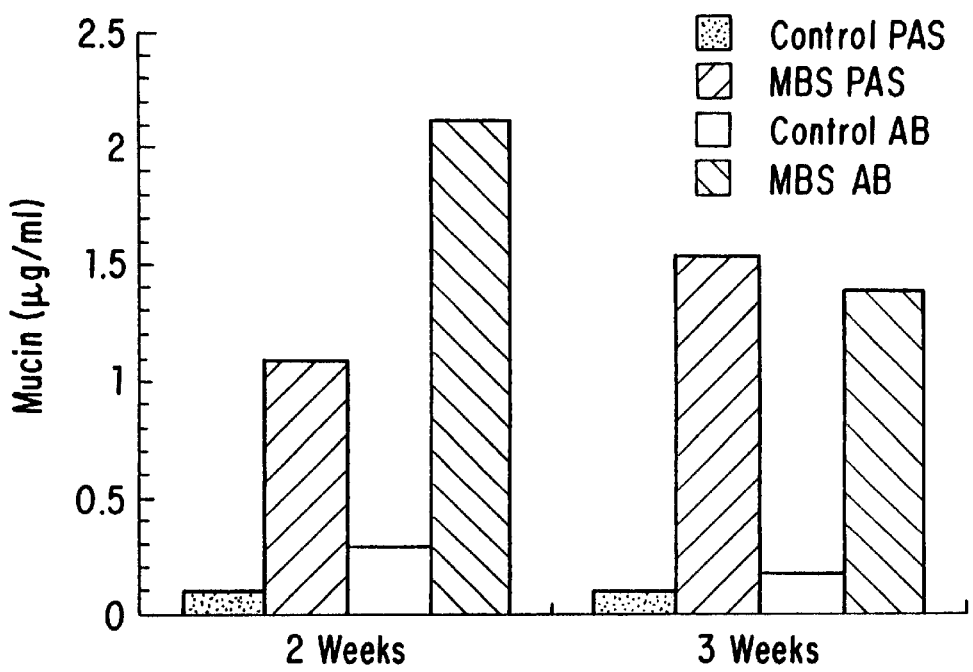

FIG. 11. Effect of sodium metabisulfite on mucus glycoprotein content in bronchiolar lavage samples. Bronchiolar lavages were performed on anesthetized rats which had been exposed to either aerosolized $H_2O$ or sodium metabisulfite for the indicated time periods. Lavage samples were obtained by pooling 3×5 ml washes using phosphate buffered saline. The samples were centrifuged to remove cellular material and a 1 ml aliquot of the supernatant was eluted on a Sepharose CL-6B column and mucus glycoproteins were measured.

Figure 12:
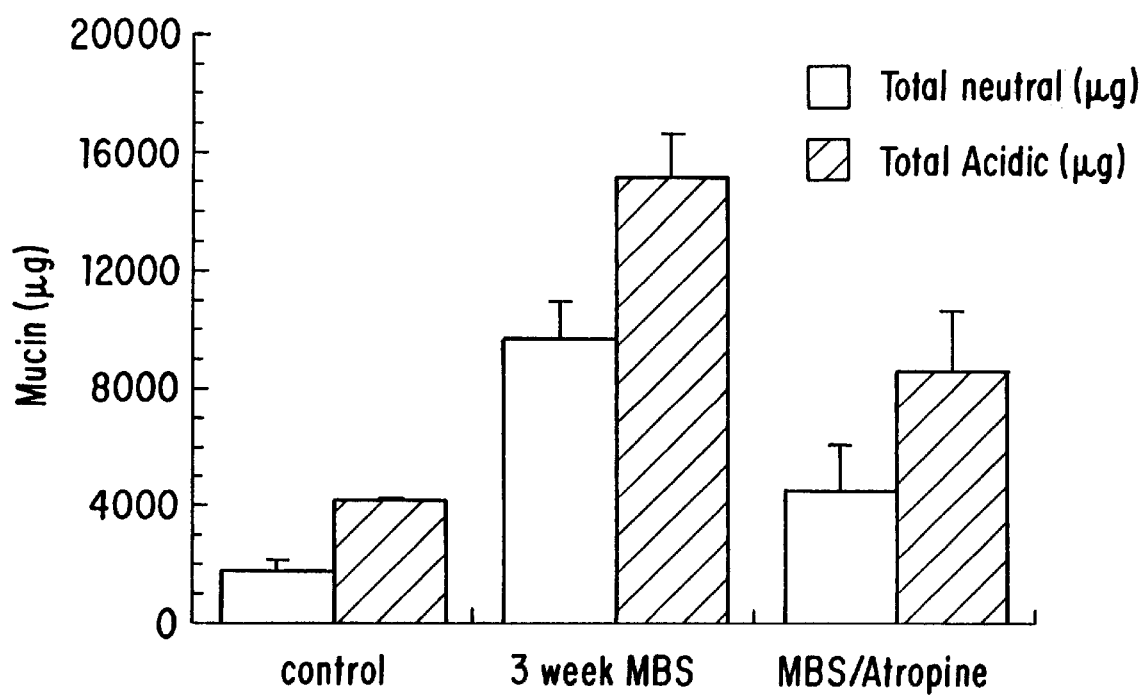

FIG. 12. Effect of atropine on rat mucus glycoprotein content. Atropine was administered to rats 30 minutes to sodium metabisulfite mist exposure.

Figure 13A:
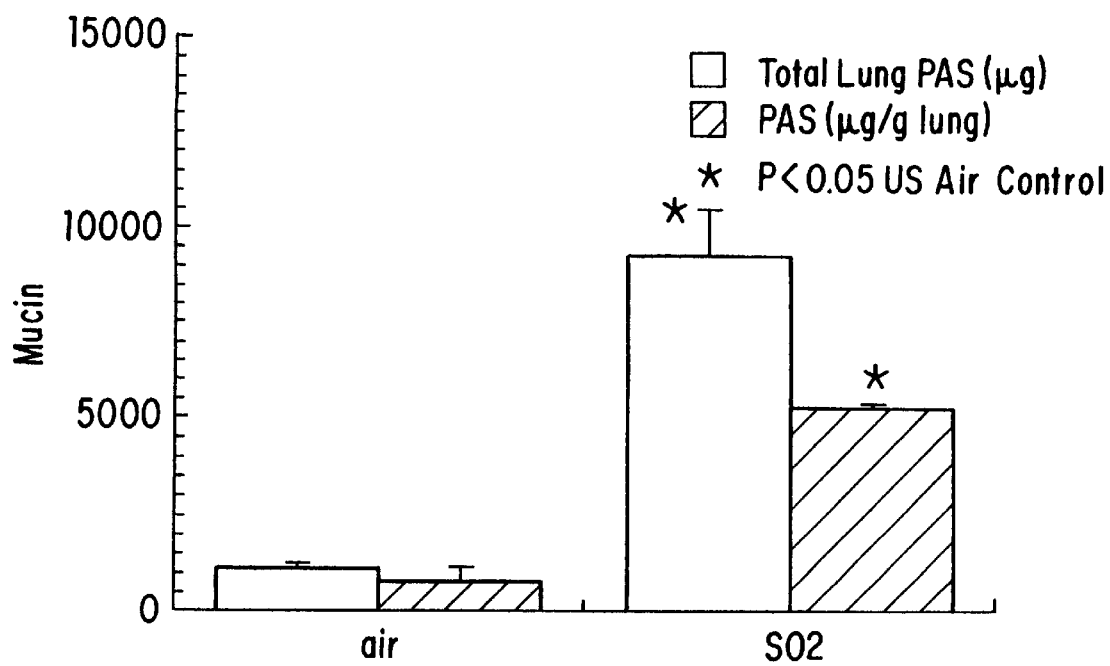
Figure 13B:
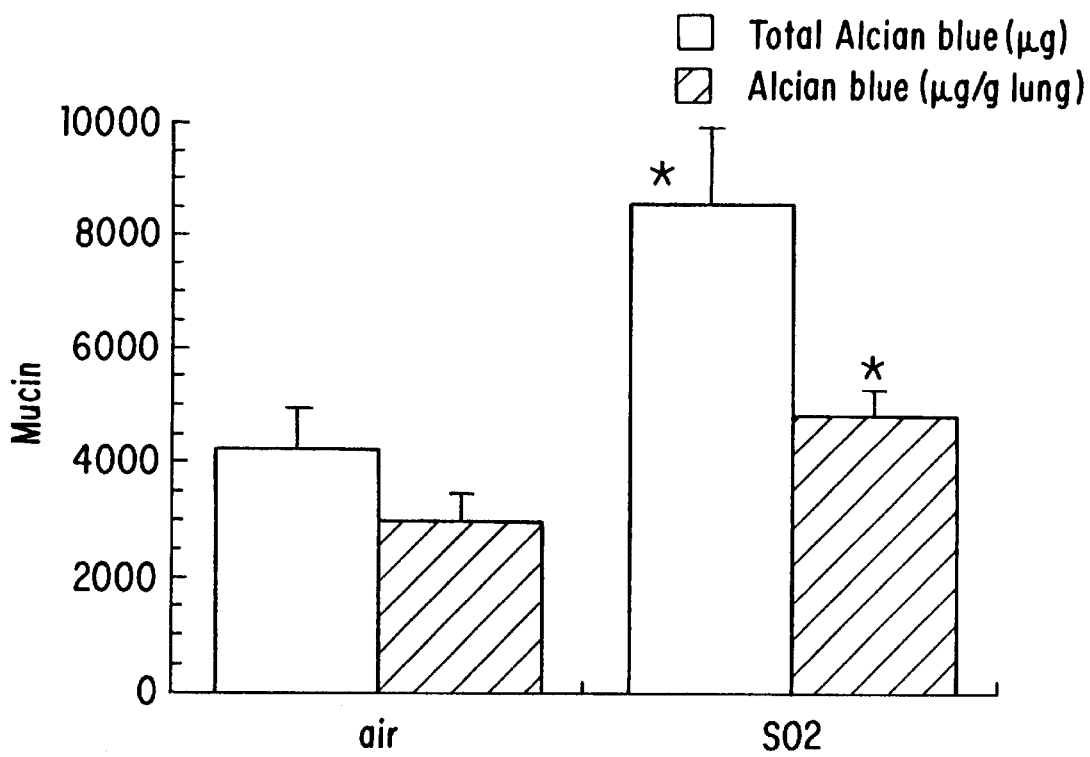

FIG. 13A and 13B. Effect of 6 weeks SO2 exposure on rat lung mucus glycoprotein content. Rats were exposed to 250 ppm SO2 gas for 5 hr/day, 5 d/wk, for 6 weeks. The neutral and acidic mucus glycoprotein content of the tissues were measured. n=6 animals for each treatment group.

Figure 14A:
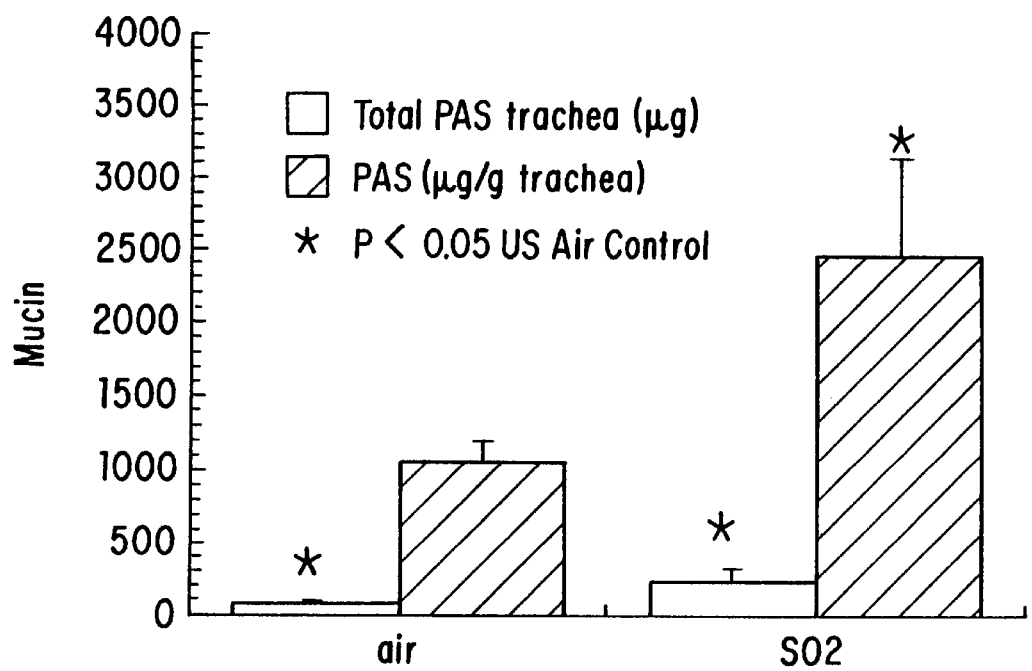
Figure 14B:
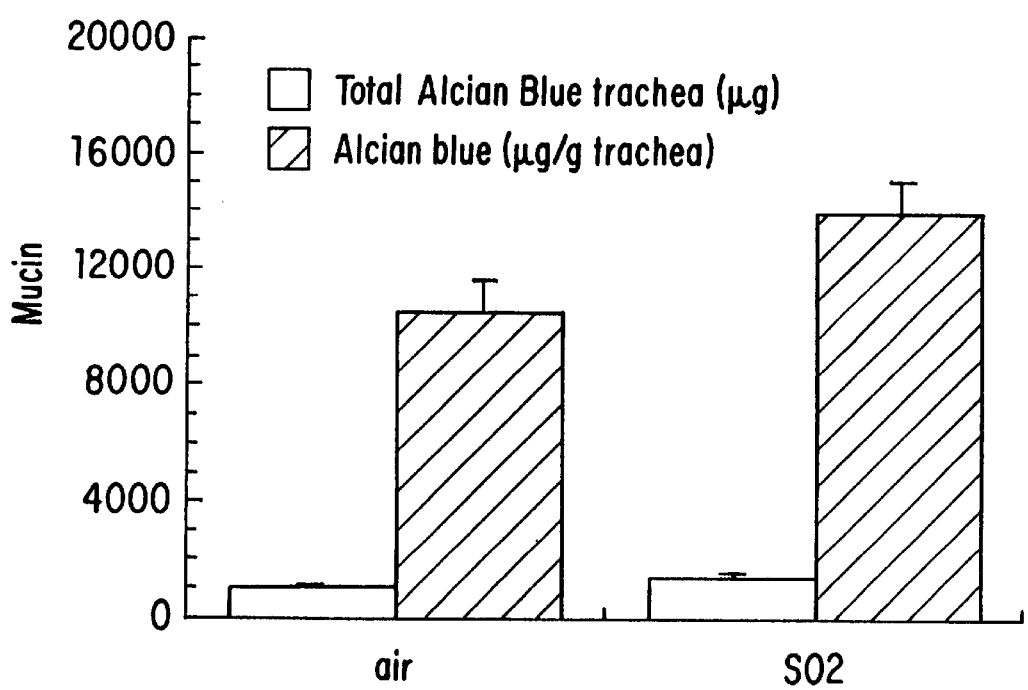

FIG. 14A and 14B. Effect of 6 weeks SO2 exposure on rat tracheal mucus glycoprotein content. Rats were exposed to 250 ppm SO2 gas for 5 hr/day, 5 d/wk, for 6 weeks. The neutral and acidic mucus glycoprotein content of the tracheae were measured. n=6 for each treatment group.

DETAILED DESCRIPTION OF THE INVENTION

This invention is a rapid and simple technique according to which the levels of acidic and neutral mucins in lung tissue may be assessed. It extends the use of PAS and Alcian blue staining from histological sections to dot-blotting on membranes such as Immobilon-P membrane. Quantitative determination of PAS positive glycoproteins in solution was first demonstrated by Mantle and Allen [Mantle, M. and A. Allen. (1978). Biochem. Soc. Trans. 6:607–609, but the method which they described required at least 2 hours incubation with periodic acid for complete sample oxidation and a further 30 minutes for color development with Schiff's solution. In addition, reagents were repeatedly pipetted for each sample tested.

The instant method uses a solid matrix on which the samples are applied, the amount of time required for complete oxidation of the sample is reduced to 5 minutes and stable color develops within 5 minutes. In addition, up to 96 samples can be tested by immersing a polyvinylidene fluoride (PVDF) membrane, such as an Immobilon-P™ membrane in the PAS reagents rather than having to accurately pipette the solutions into individual tubes.

Thornton et al. [(1989) Anal. Biochem. 182:160164], described a quantitative PAS assay that involves the blotting of mucus glycoproteins onto nitrocellulose membranes. Using a monochrome camera interfaced with a microcomputer based image analysis system, they were able to measure quantities of mucin glycopeptides as low as 0.05 μg. However, the linearity of the measurements occurred, only over a 4-fold range of concentrations. The lack of linearity in their assay may be due to the inherent lack of dynamic range in the camera used.

By making the membrane translucent with paraffin liquid or transparent with 1-heptanol or another lower alkanol (see FIG. 10), the instant invention may be carried out in a 96-well plate reader for measuring the staining intensity with linearity over a 40-fold concentration range for PAS staining and a 20-fold range for Alcian blue. Furthermore, the use of a plate reader obviates the need for a complex and expensive imaging system.

A calorimetric assay for mucus glycoproteins using Alcian blue has been reported by Hall et al. [(1980). Biochem. Soc. Trans. 8:72 (Abstr.)]. That assay is based on determinations in solution, and similar to the PAS determinations reported by Mantle and Allen, [(1978). Biochem. Soc. Trans. 6:607–609], the assay incorporates a number of centrifugation steps, as well as extended incubation times.

The method described herein only requires that the samples be applied to the membrane and stained with Alcian blue. The actual staining and destaining time required is less than 30 minutes and involves minimal pipetting of reagents.

The measurement of only HMW mucus glycoprotein in the whole lung extracts is facilitated by using the material eluting in the excluded volume of a size exclusion column such as Sepharose CL-6B gel. The PAS and Alcian blue material is confirmed to be mucus glycoprotein by the resistance of this material to enzymatic digestion with hyaluronidase and chondroitinase. The lack of Alcian blue staining in accordance with Scott and Dorling [Scott, J. E. and J. Dorling. (1965). Histochemie 5:221–233] indicates that heparin/heparan and kertatan sulphates were not present in the excluded volume. As shown by FIGS. 7A and 7B. the PAS and Alcian blue staining of material in the void volume is comprised of material larger than 250 KDa.

Figure 4:
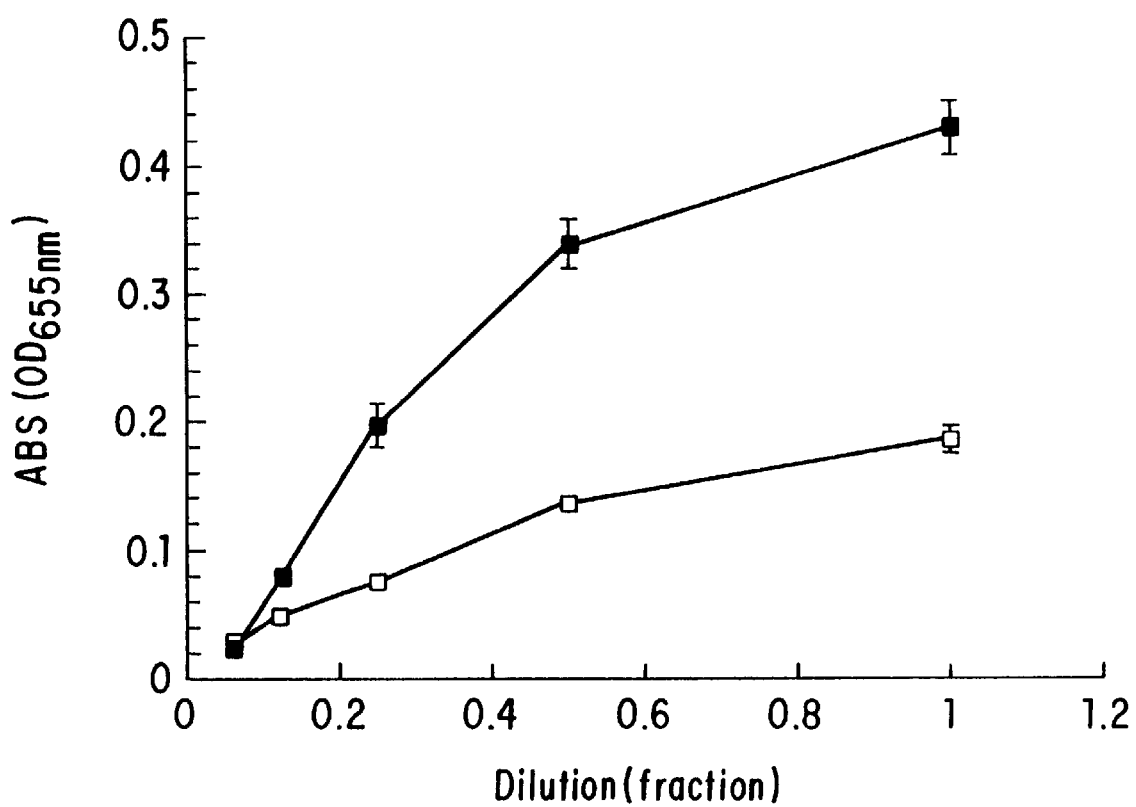
FIG. 4. Effect of sample deamination on Alcian blue staining. The void volume material obtained from a rat whole lung extracted was diluted with column buffer to the indicated fractions. The diluted samples (100 µ) were dot-blotted onto Immabilon-p™ membranes. The membranes were incubated overnight in a solution containing 2 M $NaNO_2$ and 12.5% glacial acetic acid. The membranes were washed 2×15 min in Milli-Q treated water and stained with Alcian blue and absorbencies measured. Values are means of 3 separate experiments done in duplicate ±SEM. Open symbols represent untreated membranes; closed symbols represent membranes subjected to deamination.

Under moderate reducing and dissociative conditions, a significant amount of low molecular weight protein can co-elute with the mucin. This additional protein inhibits Alcian blue staining of the mucus. The quenching of Alcian blue staining most likely results from the masking of Alcian blue binding sites on the mucin by amino groups of the contaminating proteins. We have discovered that deaminating the samples causes a shift in the sample dilution curve (FIG. 4).

Tracheal lavage samples also show the presence of contaminating proteins which interfere with mucin measurements by a fucose-specific lectin based assay. The observed nonlinear behavior of the samples upon dilution is overcome by separating the mucins from contaminating protein on a size exclusion column such as Sepharose CL-6B gel under dissociative conditions.

The usefulness of this assay for examining changes in mucin content in airways of animal models for hypersecretion is demonstrated by exposing the lungs of rats to metabisulfite. The amounts of total neutral and acidic mucin measured in control lungs was found to be 1.1 mg and 6.1 mg mucin, respectively. The ratio of acidic/neutral mucin (5.5:1) is in agreement with that secreted from tracheal explants of rats (4.2:1) [Kaizu, T., et al. (1978). Comp. Biochem. Physiol. 62B:195–200], and measured using differential staining of histological sections (2:1) [Sturgess, J. and L. Reid. (1973). Br. J. Exp. Path. 54:388–403].

We have further refined the foregoing methodology for the measurement of both acidic- and neutral-mucoglycoproteins in a manner that allows for more sensitivity and specificity than previously available.

In one embodiment, soluble protein is extracted from whole rat lung and is incubated with 0.1% SDS and 10 mM mercaptoethanol. The sample is applied to and eluted from a Sepharose CL-6B column. The material eluting in the void fraction of the column contains considerable levels of low molecular weight protein when assessed by Coomassie blue staining of void volume material which had been subjected to SDS-PAGE and electroblotted onto PVDF membranes. Alcian blue staining of PVDF membranes on which the same material was electroblotted from SDS-PAGE shows that 50–60% of total stainable material is of high molecular weight (HMW) (>205 kD).

In order to exclusively stain only HMW material, we established conditions that allow for the dissociation of low molecular weight (LMW) proteins from HMW proteins eluting in the column void volume. Aliquots of airway extract are incubated with 10 mM mercaptoethanol and increasing concentrations of SDS from 0.1% to 2.0%. The samples are heated at 68° C. for 2 min. and then chromatographed on Sephacryl S300 HR in a water-jacked column maintained at 37° C. Protein eluting from the column is monitored at 280 nm. The amount of protein eluting in the void fraction decreases with increasing concentrations of SDS as judged by the peak height in the elution profile. Since mucus glycoproteins do not exhibit an absorbance at 280 nm, these results indicate that non-mucin LMW proteins were not co-eluting with the HMW mucus glycoproteins. This conclusion is further supported with results obtained by Coomassie Blue staining of the void volume material following SDS-PAGE. The amounts of LMW protein (<205 kD) eluting in the void volume is reduced with progressive increases in SDS. The amounts of HMW mucus glycoprotein are not affected to any significant extent where the same void volume fractions were electrophoresed on 2% agarose gels, transferred to PVDF membranes and stained with either PAS or Alcian blue.

We attempted to use other ionic and non-ionic detergents rather than SDS, but these detergents failed to provide the disociative properties required for the partial purification of mucus glycoproteins from the airway extracts.

When compared to the same samples treated with 0.1% SDS, those samples incubated with 2.0% SDS exhibit greater differences in extracts prepared from animals exposed to $SO_2$ relative to air exposure. These differences most likely result from the reduction of LMW proteins eluting in the void volume fraction of the column which can react with PAS or Alcian blue stains. Thus. in a preferred embodiment of this invention, airway extracts are treated with about 2% SDS prior to size fractionation of the extract and immnobilization.

The total amounts of mucin measured in the airways by our assay may be an underestimation of true mucus glycoprotein content throughout the airway tissue. The lack of a radiolabelled mucin probe makes it difficult to estimate how much mucus glycoprotein is associated with the particulate matter that is discarded following centrifugation. Nevertheless, the hypotonic buffer employed for mucin extraction is clearly 4-fold more efficient compared to an isotonic medium. This difference may be due to more favorable conditions for rupturing and emptying of cells and of secretory granules that contain mucus glycoproteins. Despite this difficulty, it is clear that the measured increases in total mucin (hypertrophy, hyperplasia) and mucin per gram of tissue (hyperplastic) are consistent with the observed histological changes. Determining whether a one to one relationship is preserved between the measured mucin and morphometrical determinations would require examination of every section of tissue and determination of the mucin content for every cell. However, Lamb and Reid [(1968). J. Path. Bact. 96:97–111], using combined PAS/Alcian blue staining of histological sections, reported changes throughout the airways which are similar to our measured changes. Those researchers used $SO_2$ rather than metabisulfite mist, but the active component in metabisulfite mist is reported to be $SO_2$ gas [Fine, J. M., et al. (1987). Am. Rev. Respir. Dis. 136:1122 1126] and therefore similar changes may be anticipated with the two irritants. While bronchoconstriction in guinea pigs following exposure to metabisulfite mist has been described [Lotval, J. O., et al. (1990) (1990). Am. Rev. Respir. Dis. 142:1390–1395], the use of metabisulfite as an inducer of metaplastic changes has not been reported.

$SO_2$ is an agent common to both cigarette smoke and urban air pollution. Basbaum and coworkers [(1991), Biochem. Biophys. Res. Comm. 181:1–8] have shown that exposure of rats to $SO_2$ causes an increase in mucin gene transcription, mucoprotein expression, and transdifferentiation of nonmucus containing cells into cells which produce and secrete mucus. An obvious drawback to the use of $SO_2$ as a mucus cell inducing agent in small laboratory animals is its inherent toxicity to man. The safe handling and use of gas cylinders that contain concentrated $SO_2$ requires special precautions and facilities which may preclude certain institutions from employing this agent for developing animal models. Fine et al. [(1987). Am. Rev. Respir. Dis. 136:1122 1126] have shown that sodium metabisulfite solution at pH 3.5 liberates $SO_2$ gas. The levels of $SO_2$ generated from a 1% sodium metabisulfite solution was measured to be greater than 5 ppm, the upper limit of detection. Because of the ease of handling of this inducer, it is a superior compound for this purpose.

This assay can therefore be used successfully, just as with mucus glycoprotein specific antibodies and cDNA probes, as an index of hypertrophic and hyperplastic changes.

Thus, this invention is an assay useful for the measurement of animal airway mucus glycoprotein content. The assay is rapid, simple, and does not require probes which may be species and model specific. The assay is particularly useful for investigators wishing to study neurobumoral components involved in upregulated mucus glycoprotein expression in small animal models of chronic obstructive pulmonary disease.

One embodiment of the invention is a method for the rapid estimation of hyperplastic and hypertrophic changes in animal airways, in which acidic and neutral mucoproteins are specifically measured, which comprises the steps of:

a) exposing a test animal to a suspected metaplastic inducer;
b) removing the lungs of the test animal and homogenizing the lungs in an appropriately buffered hypotonic solution containing reducing agents and protease inhibitors;
c) removing particulate matter and size-fractionating the soluble extract;
d) immobilizing the high molecular weight material;
e) staining the immobilized material for either acidic or neutral mucosubstances; and
f) quantitating the specific staining.

Another embodiment of the invention is a method for quantitation of glycoproteins requiring 5 minutes for complete oxidation and 5 minutes for stable color development for PAS staining and 30 minutes for Alcian Blue staining which comprises:

a) blotting high molecular weight glycoprotein containing samples on a membrane;
b) Deaminating the blotted material;
c) Staining with PAS or Alcian Blue;
d) Rendering the membrane translucent with paraffin liquid or transparent with a lower alkanol selected from 1-heptanol, dodecanol, and octanol liquid (1-heptanol is preferred, see FIG. 10); optimally, after rendering the membrane transparent, the membrane is dipped in paraffin liquid which keeps the membrane transparent, probably by retarding the evaporation of the more volatile alkanol; and
e) Quantitating the PAS or Alcian Blue specific staining.

A further embodiment of the invention is a method for the estimation of hyperplastic and hypertonic changes in animal airways, in which ecidic and neutral HMW mucoproteins are specifically measured, which comprises the steps of:

a) exposing a test animal to a suspected metaplastic inducer;
b) removing the lungs of the test animal and homogenizing the lungs in an appropriately buffered hypotonic solution containing reducing agents, protease inhibitors and SDS;
c) removing particulate matter and size-fractionating the soluble extract;
d) immobilizing the high molecular weight material;
e) staining the immobilized material for either acidic or neutral mucosubstances: and
f) quantitating the specific staining.

The following examples are provided to further describe the invention, without limiting the invention to the specifics thereof. In the examples which follow, the following apply unless indicated otherwise:

Materials and Methods
Animals

Pathogen-free male Fisher 344 rats weighing 250–300 g were obtained from Charles River Breeders (Que, Can) and used within 3 days of arrival. They were housed in pathogen-free quarters and maintained on rodent laboratory chow with free access to food and water.

Chemicals and Enzymes

Periodic acid solution, Schiff's reagent, mucin (type I, III), and chondroitinase AC and ABC were purchased from Sigma Chemical Co. (St. Louis, Mo.). Sepharose CL-6B was obtained from Pharmacia (Montreal, QUE) and Alcian Blue 8GX was from Allied Chemical (Morristown, N.J.). DL-Dithiothreitol (DTT), leupeptin, sodium metabisulfite, and ethylenediaminetetraacetic acid (EDTA) were also purchased from Sigma. Sodium azide was purchased from Aldrich Chemical Co. (Milwaukee, Wis.) and benzamidine was from Calbiochem Corp. (La Jolla, Calif.). Bovine albumin (fraction V) (BSA) was purchased from Gibco Laboratories (Grand Island, N.Y.). Paraffin liquid was from BDH (Montreal, QUE). All other chemicals were obtained from regular commercial sources and were of reagent grade.

EXAMPLE 1

Exposure of Rats to Metabisulfite

The animals were placed in Plexiglas chambers and exposed for 3 weeks to either a mist of Milli-Q treated water or a solution containing 10% (w/v) $Na_2S_2O_5$; pH 2.5. Animals were exposed for 1 h ×5 days for the first week, 1.5 h×5 days for the second week, and finally 2 h×5 days for the last week. All rats were maintained in pathogen-free conditions for the duration of the exposure and sacrificed 5 days following the last metabisulfite treatment.

Exposure of Rats to $SO_2$

The animals were placed in Plexiglas chambers and exposed to $SO_2$ gas (250 ppm) 5 hr/day, 5 days/wk, for 6 weeks. All rats were maintained in pathogen-free conditions for the duration of the exposures and sacrificed 4 days following the last exposure.

EXAMPLE 2

Extraction of Mucus Glycoproteins From Rat Airway Tissue

The animals were anesthetized with an intraperitoneal injection of sodium pentobarbital (65 mg/kg). The trachea and lungs were quickly removed and separately polytronned (40 sec) in an ice-cold solution (1.5 ml/trachea; 5 ml/g lung tissue) which contained (in mM): $NaH_2PO_4$, 20; EDTA, 2; DTT, 10; 0.05% sodium azide and 1 mg/ml leupeptin; pH 7.4. Soluble protein was obtained by centrifuging the whole homogenate at 39,000×g for 60 minutes in a Sorval RC-5B centrifuge at 4° C. The supernatants were separated from the membrane pellets and stored at −70°C.

EXAMPLE 3
Sepharose CL-6B Chromatography of Rat Airway Extracts

A 1 ml aliquot of the supernatant obtained as in Example 2 was quickly thawed in the presence of 0.1% SDS and 10 mM mercaptoethanol and applied to a column (1.0×20 cm) packed with Sepharose CL-6B gel and equilibrated with running buffer. A Bio-Rad AS-100 HRLC automatic sampler was used to inject airway extract samples onto the column. The sample(s) was eluted from the column with phosphate buffered saline containing 0.05% sodium azide, 10 mM DTT and 2 mM EDTA; pH 7.4. Column fractions were collected at a rate of 0.5 ml/minutes, and monitored for protein at 280 nm using a UV-2 Pharmacia flow cell and chart recorder. The column was calibrated by determining the elution volumes for Dextran Blue 2000 (Pharmacia) and gel filtration standards obtained from Bio-Rad Laboratories (Richmond, Cailf.). All column chromatography was performed in a refrigerated cabinet maintained at 40° C.

Rat whole lungs were removed from the animals and cleared of non-airway tissue. Homogenization was carried out in a hypotonic buffer containing reducing agents and protease inhibitors as described in Example 2. Four-fold greater recovery of mucus glycoprotein from the lungs was achieved using a hypotonic buffer versus a phosphate-buffered saline solution.

Figure 2A:
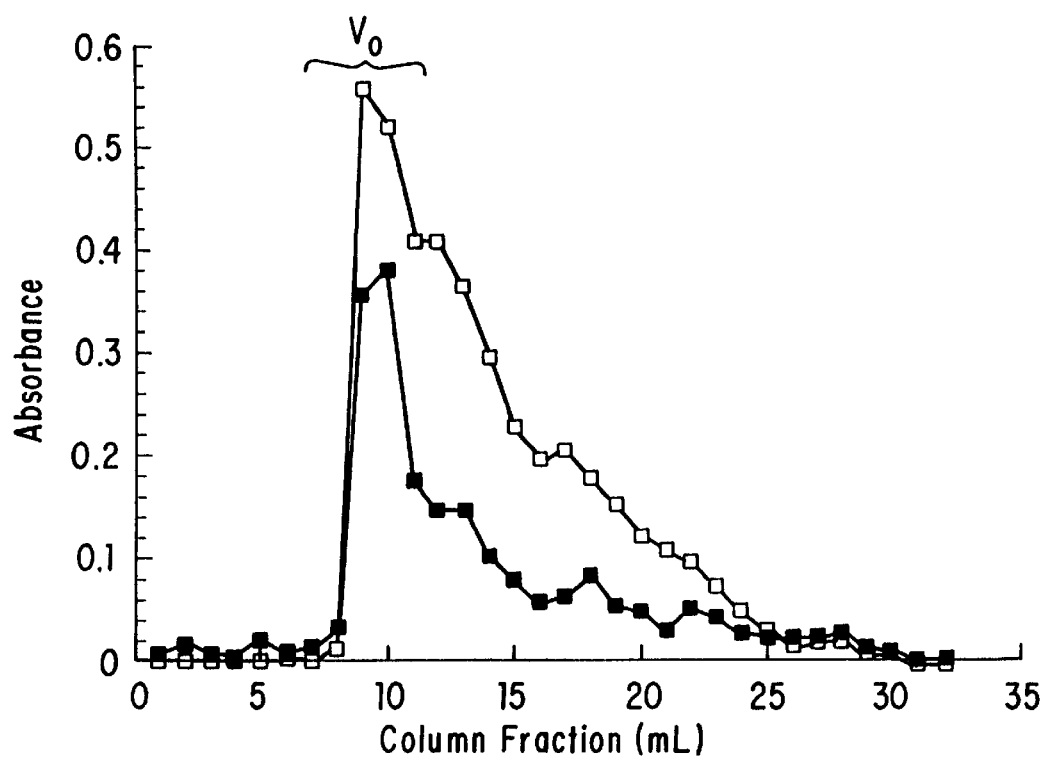
FIGS. 2A and 2B. Sepharose CL-6B chromatography of rat whole lung extracts. An extract was prepared by polytronning a rat whole lung in a solution (5 ml/g tissue) containing in mM, $NaH_2PO_4$,20; EDTA, 2; and DTT, 10; and 0.05% sodium azide and 1 mg/ml leupeptin; pH 7.4. An aliquot of the extract (1 ml) was eluted from the column (1.0×20 cm) with phosphate-buffered saline containing 10 mM DTT, 0.05% sodium azide, and 2 mM EDTA, pH7.4. Fractions (1 ml) were collected at a flow rate of 0.5 ml/minutes. Column fractions (100 µl) were dot-blotted onto Immobilon-P membranes and stained with either PAS (closed squares) or Alcian blue (open squares). Absorbencies were measured. The exclusion volume of the column was determined using Dextran Blue 2000. Column calibration was carried out using proteins of known molecular size (inset).
Figure 2B:
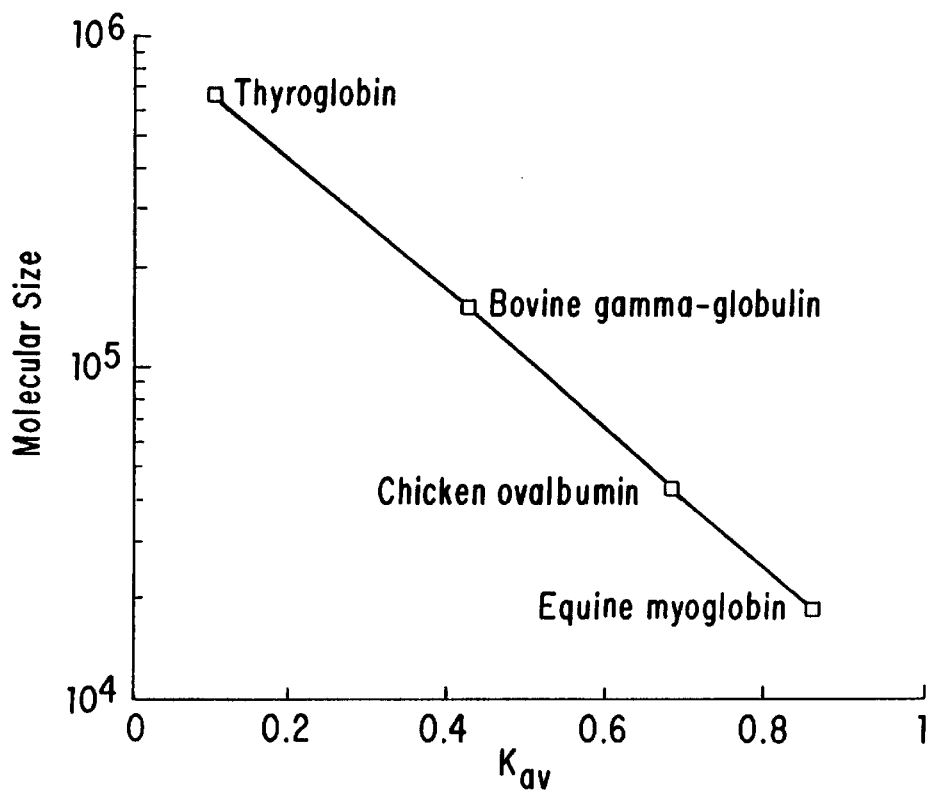

Alcian blue and PAS staining (see example 4) of membranes blotted with fractions eluting from the column reveals a high concentration of glycoprotein in the void volume of the column with some glycoprotein in the trailing fractions. The molecular size for material eluting in the void fraction is estimated to be in excess of 670,000 daltons as calculated from the elution profiles of known standards and Dextran blue 2000 (FIG. 2A and 2B).

Figure 3A:
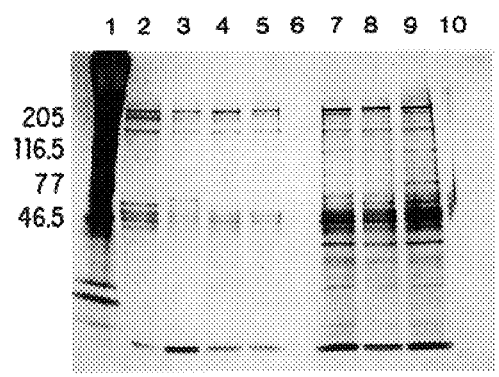
FIG. 3A and 3B. SDS polyacrylamide gel electrophoresis of airway extract material eluting in the column void volume. Samples obtained from the void volume of Sepharose CL-6B chromatographed airway extracts were incubated in a buffer containing 2% SDS with 10 mM mercaptoethanol at 100° C. for 4 min. Samples were loaded onto 4–20% Tris-glycine acrylamide gels and electrophoresed at 200 V for 2 h. Gels were washed 3×15 minutes and fixed with a solution containing 40% methanol (v/v) and 10% acetic acid (v/v). Gels were stained with either Coomassie blue (panel a) or Alcian blue (panel b). Lane 1) protein stds.; lanes 2 to 5) control rats; lanes 7–9) metabisulfite exposed rats.
Figure 3B:
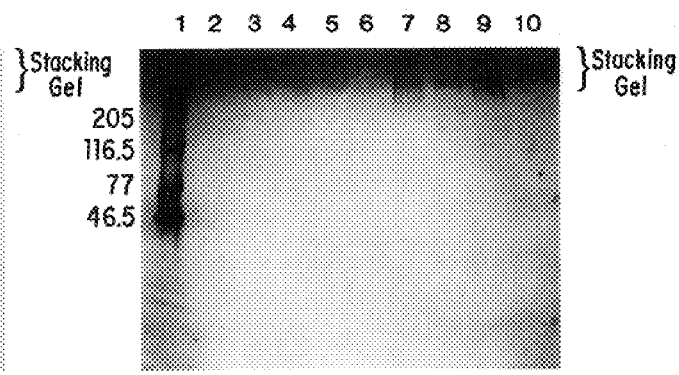

To determine whether the PAS and Alcian blue reactive material eluting in the void volume was comprised of high molecular weight (HMW) macromolecules and/or large aggregates of smaller molecules, the material contained in the void volume was subjected to SDS electrophoresis on 4–20% polyacrylamide and 2% agarose gels. Polyacrylamide gels stained with Coomassie blue exhibit a considerable amount of protein in lanes where samples prepared from the void fraction were loaded (FIG. 3a). Gels which were loaded with the same samples and stained for glycoprotein with Alcian blue showed no positive staining of material in the size range of 250 KDa and lower (FIG. 3b). Staining was observed for HMW glycoprotein in the stacking region of the gel. Results obtained with PAS staining were similar to those of Alcian blue. These results indicate that under moderate reducing (10 mM DTT and mercaptoethanol) and dissociative conditions (0.1% SDS), extracted lung material excluded from the Sepharose CL-6B gel is made up of HMW macromolecules which stain PAS and Alcian blue positive and co-elutes with lower molecular weight proteins which are undetectable with glycoprotein sensitive stains when subjected to SDS PAGE.

EXAMPLE 4
Ouantitation of Airway Mucins by PAS and Alcian Blue Staining

Determination of Alcian Blue and PAS positive material was performed by applying the mucin standards or column fractions (25–100 μl) to a prewetted Immobilon-p™ membrane (Millipore, Bedford, Mass.) using a 96 well Dot-Blot filtration apparatus from Gibco (Burlington, ONT) under a vacuum of 300 mm Hg. Each well was washed 2 times with 250 μof a solution containing 50 mM sodium bicarbonate. The membrane was removed from the apparatus and washed 2×5 minutes in Milli-Q treated water. In order to quantitate Alcian Blue reactive material, the membrane was incubated in a 5% (w/v) solution of BSA for 5 minutes. The membrane was then washed 2×5 minutes in Milli-Q treated water and transferred into a hybridization bottle (Gibco) which contained an Alcian blue dye solution (1 g Alcian Blue 8GX/100 ml 3% (v/v) acetic acid; pH 2.5). Following a 5 minutes incubation, the membrane was removed from the bottle and washed 3×5 minutes with Milli-Q water. The membrane was dried in the dark and made transparent by immersion in 1-heptanol.

Rendering Immobilon-P Membranes Transparent with Solvents

In order to facilitate the quantitation of dot-blotted Alcian blue and PAS positive material on the Immobilon-P membrane with a 96-well plate reader, different solvents were tried to render the membrane transparent (FIG. 10). By wetting the membranes with paraffin liquid, the membrane became translucent with measured absorbencies of 0.65 and 0.81 O.D. units at 655 nm and 550 nm, respectively. Staining of known mucin standards with background absorbencies in this range results in an extremely poor signal to noise ratio of approximately 1:1. Short chain alcohols such as dodecanol, octanol and heptanol significantly reduced the measured background absorbencies of the membrane and consequently increased the signal to noise ratio of the staining measurements to 8:1 with heptanol. Heptanol is preferred over dodecanol because of the tendency of the latter to crystallize at room temperature. Heptanol is also preferred over the shorter chain alcohols because of their volatility, and the observation that ethanol actually dissolves the membrane. After rendering the membrane transparent with one of these lower alkanols ($C_5$–$C_{12}$), the membrane is dipped in paraffin liquid. This maintains the membrane in a transparent state, probably by retarding evaporation of the volatile lower alkanol, long enough to allow the quantitation to proceed without changes in background signal.

Ouantitation

The membrane was placed face-down on the bottom of a 96-well flat bottom ELISA plate and the optical density of Alcian blue staining was measured at 655 nm with a BioRad plate reader. Quantitation of Alcian blue reactive material was achieved by comparing the sample optical density against that for known amounts of bovine submaxillary gland mucin (Sigma type-I). Staining for heparin/heparan and keratan sulphates was performed as described by Scott and Dorling [(1965) Histochemie 5:221–233]. Briefly, membranes were treated in a similar fashion as that for Alcian blue with the exception that the Alcian blue dye solution was replaced by one which contained 0.05 g Alcian blue in 200 mM acetate buffer and containing 60 mM to 900 mM $MgC_2$.

PAS positive material was determined by applying the mucin standard and column fractions to the Immobilon-P membrane as described above. The membrane was washed 2×5 minutes in Milli-Q treated water and then placed in a hybridization bottle containing 50 ml of periodic acid solution. Following a 5 minutes incubation, the membrane was washed 2×5 minutes in Milli-Q treated water, dried, and placed into another hybridization bottle containing 50 ml of Schiff's reagent and incubated for an additional 15 minutes. The membrane was then washed 3×5 minutes with a 5% sodium metabisulfite solution in an airtight container and rinsed for 3×5 minutes with Milli-Q water. After drying, the membrane was made transparent with 1-heptanol and the level of PAS staining was measured as described above at 550 nm. Quantitation of PAS positive material in the column fractions was determined by using porcine stomach mucin (Sigma type-III) as a standard.

Alcian Blue and PAS Quantitation of Mucin Standards

Figure 1A:
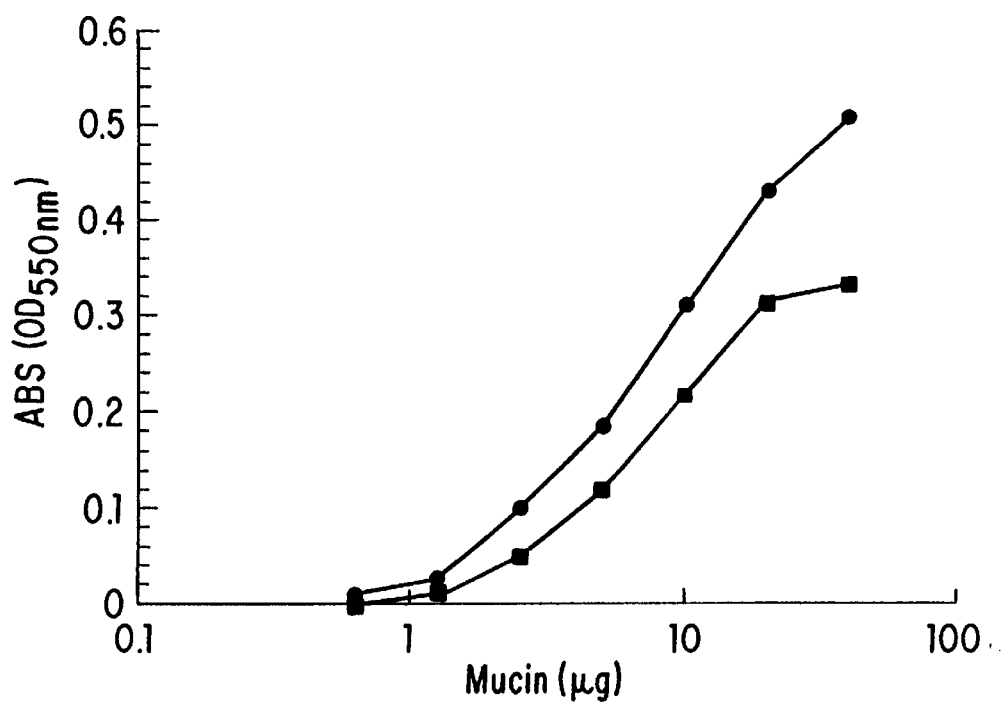
FIGS. 1A and 1B Alcian blue and PAS quantitation of mucin standards. Indicated amounts of porcine stomach mucin (1% sialic acid content)(circles) and bovine submaxillary mucin (5% sialic acid content)(squares) were dot-blotted onto an Immobilon-p™ membrane. The membranes were stained with either PAS (panel a) or Alcian blue (panel b). The stained membranes were made transparent by wetting with 1-heptanol and absorbencies measured using a 96-well Bio-Rad plate reader. Each point represents the mean of triplicate determinations.
Figure 1B:
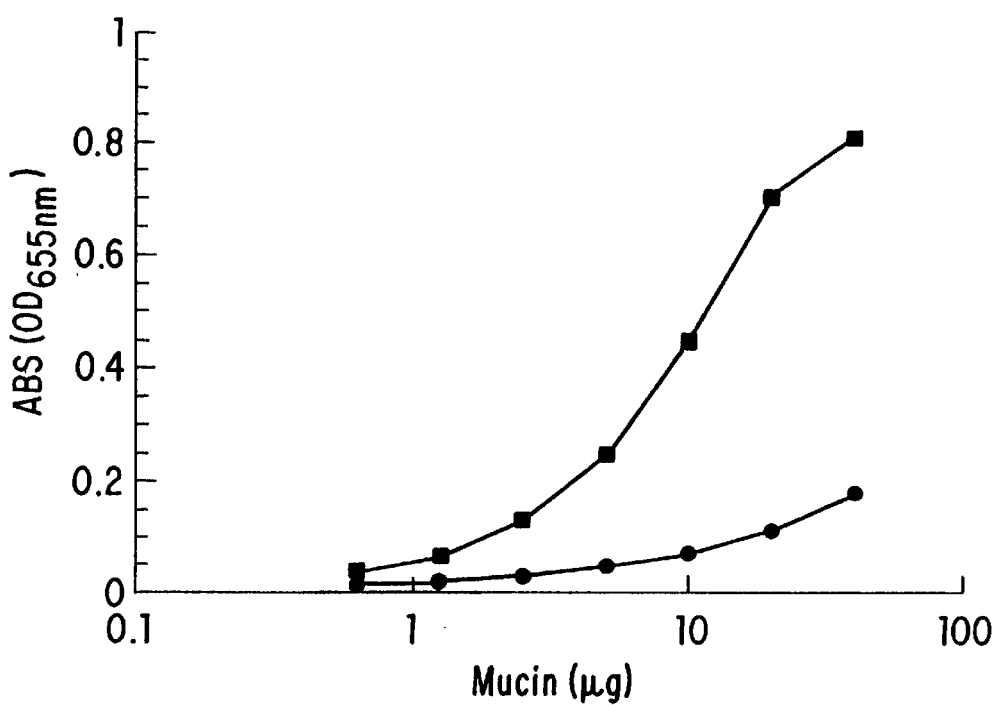

Alcian blue and PAS staining was carried out on Immobilon-P membranes that had been blotted with known amounts of purified mucin. Membranes stained with PAS exhibited preferential staining for mucin purified from porcine stomach (PSM) over bovine submandibular gland mucin (BSGM). The staining intensity of PSM was approximately 2-fold greater than that for BSGM in dots where 0.5 $\mu$g to 10 $\mu$g of mucin were applied (FIG. 1a). PAS staining of PSM was linear from 0.5 $\mu$g to 20 $\mu$g. A linear fit for Abs. vs. $\mu$g mucin ($\mu$g mucin=0.1+19.4×O.D.) was observed for all standard curves generated. When membranes were stained with Alcian blue, the BSGM was exclusively stained compared to the PSM over a range from 0.5 $\mu$g to 10 $\mu$g (FIG. 1b). Linearity for Alcian blue staining of BSGM was observed over the same range and was routinely fitted in a linear fashion ($\mu$g mucin=0.46+25.9×O.D.). These data indicate that mucins of varying acidity are stained differentially by Alcian blue and PAS. Neutral mucins are preferentially stained by PAS whereas the mucins with higher sialic acid or sulfate are stained by Alcian blue. Several types of blotting membranes were examined for their capacity to bind mucin. Although the number of membranes examined was not exhaustive, it was concluded that Immobilon-P exhibited the physical stability and mucin binding capacity that would allow for consistent staining and quantitation of blotted mucins.

EXAMPLE 5

Deamination of Dot-Blotted Proteins

Mucin standards and/or airway extracted material excluded from Sepharose CL-6B gel chromatography, were dot-blotted onto Immobilon-P membranes as described above. The membranes were washed 2×5 minutes in Milli-Q treated water and then incubated overnight in a solution containing 2 M $NaNO_2$ and 12.5% glacial acetic acid (v/v). The membranes were washed 2×15 minutes with Milli-Q treated water before staining with PAS or Alcian blue as described in Example 4.

Effect of Sample Deamination on PAS and Alcian Blue Staining

In order to align the staining intensity of the excluded airway material to within the linear range of the mucin standards, serial dilutions of the samples were made. It was observed that a given dilution factor did not result in the same corresponding decrease in measured absorbence for Alcian blue staining. Since the airway mucin samples were associated with significant amounts of extraneous protein it was possible that charged amino groups present on those proteins were interfering with the mucin determinations. As shown in FIG. 4, a sample dilution of 1:2 does not result in a 50% reduction in Alcian blue absorbence. Further dilutions of 1:4 to 1:16 did not result in corresponding decreases in the measured absorbencies. Although the Alcian blue staining appeared to decrease proportionally with the dilutions, underestimations of mucin unknowns were possible when extrapolating from the standard curve. Deamination of the membranes resulted in a shift in the slope of the sample curve towards that obtained for the purified mucin standards. Measurements of sample mucins by PAS staining were not appreciably affected by the deamination process. An enhancement in Alcian blue staining of the BSGM mucin standard was also observed following the deamination process. This may be due to the presence of low molecular weight proteins found in the commercially available mucin.

EXAMPLE 6

Glycoconjugate Analysis

Brain and airway tissue was removed from animals, homogenized and subjected to centrifugation as described in Example 2. Following Sepharose CL-6B chromatography, the void volume fraction was examined for the presence of proteoglycans by treatment with specific enzymes. One milliliter aliquots were adjusted in 5% v/v acetic acid to the appropriate pH used for the enzymatic digestion and treated separately with hyaluronidase (30 U/ml) at pH 7.0 and 37° C. for 24 hours; chondroitin AC lyase (0.4 U/ml) at pH 7.3 and 37° C. for 24 hours. A control was maintained at pH 7.4 and 37° C. for 24 hours. The enzyme digests were then chromatographed on a Sepharose CL-6B column and amounts of Alcian blue reactive material were quantitated as described in Example 4.

Figure 5A:
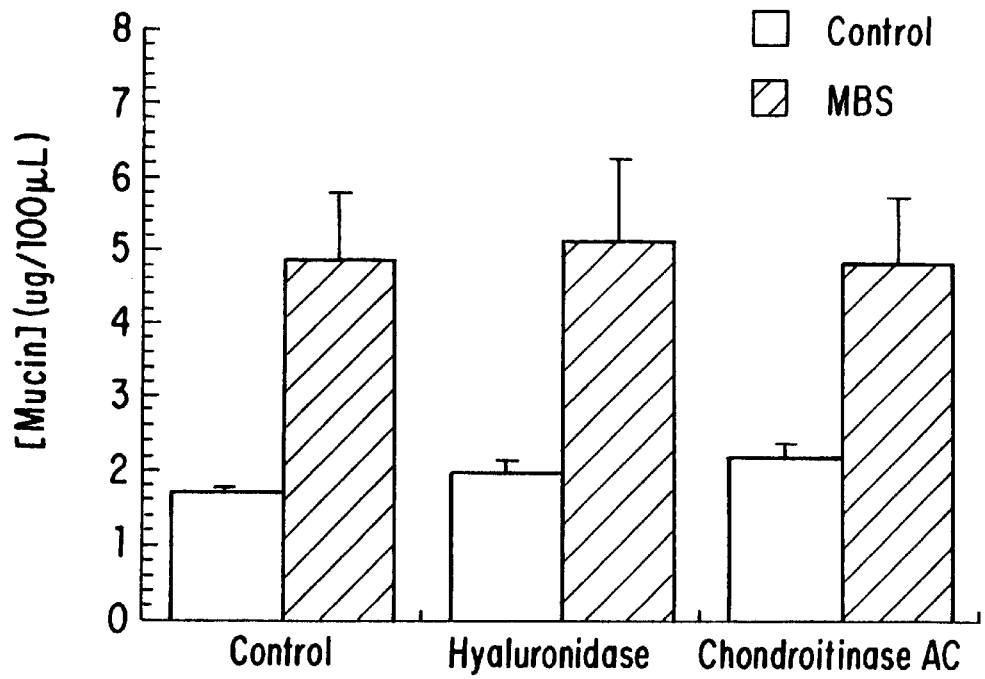
FIG. 5A and 5B. Enzymatic digestion of void volume material. Extracts of rat whole lung (control and sodium metabisulfite exposed) were prepared and chromatographed on a Sepharose CL-6B column as described in FIG. 2.
Figure 5B:
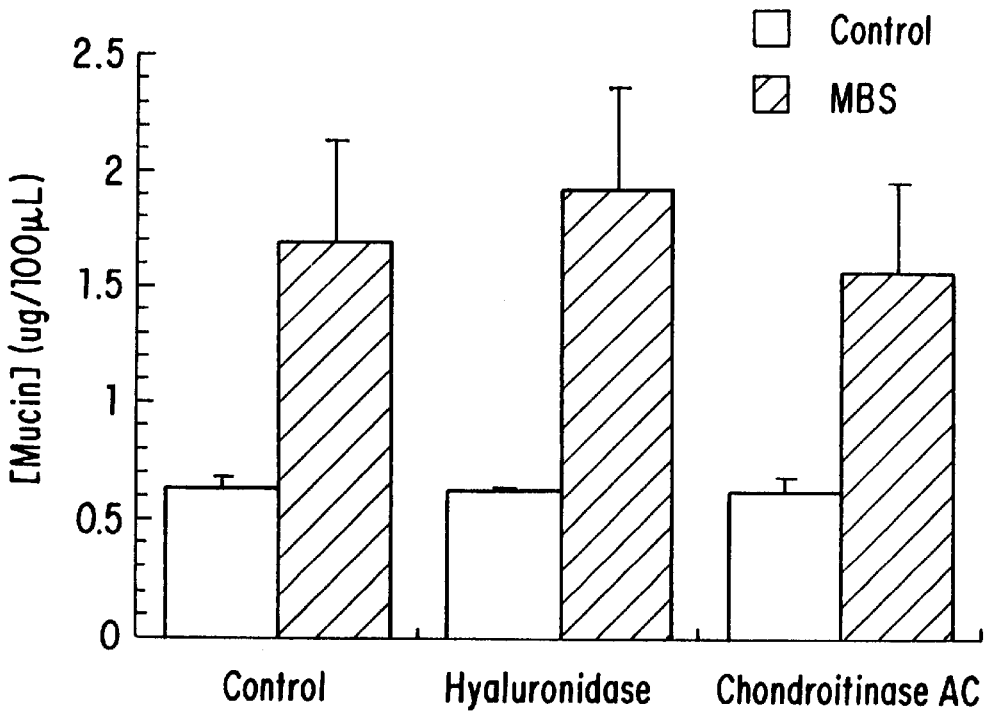

Incubation of airway material with hyaluronidase or chondroitinase had no significant effect on the amount of either PAS or Alcian blue reactive material in the excluded fraction (FIG. 5). Material extracted from rat brain and eluting in the exclusion volume of the column was degraded by incubation with hyaluronidase and chondroitinase indicating that appropriate incubation conditions were used. The possible presence of heparin and keratan sulphates was tested by Alcian blue staining involving the critical electrolyte concentration technique described by Scott and Dorling [Scott, J. E. and J. Dorling. (1965). Histochemie 5:221–233]. No Alcian blue staining above background levels was measured at $MgCl_2$ concentrations greater than 0.7 M indicating the absence of both heparin/heparan and keratan sulphates in the excluded lung extract. This confirms that material excluded from the Sepharose CL-6B gel is made up of HMW mucus glycoproteins that is stained by PAS and Alcian blue when dot-blotted onto Immobilon-P membrane. Smaller non-PAS and non-Alcian blue staining proteins are however associated with the eluted material.

EXAMPLE 7

SDS Polyacrylamide (PAGE) and Agarose Gel Electrophoresis (AGE) of Mucus Glycoprotein SDS polyacrylamide electrophoresis was carried out in 4–12% precast Tris-glycine acrylarnide gels using a Novex slab gel apparatus. Samples were incubated in buffer containing 2% SDS with 10 mM mercaptoethanol at 100° C. for 4 minutes. Samples (70 $\mu$l) were electrophoresed in the gels using the Laemmli buffer system (15) at 100 V for 2 hours. Gels were washed 3×15 minutes and fixed with a solution containing 40% (v/v) methanol and 10% (v/v) acetic acid. Proteins were stained with Coomassie brilliant blue R250, or Alcian blue. Samples were also electrophoresed in 2% Tris-glycine agarose gels using a Novex slab gel apparatus using the Laemmli buffer system. Staining of mucus glycoproteins was carried out by transferring proteins to Immobilon-p™ membrane at 30 V for 12 h in a Towbin buffer [Towbin, H., et al. (1979). Proc. Natl. Acad. Sci. USA. 76:4350–4354] using a Bio-Rad transblot apparatus. Mucus glycoproteins were visualized by staining the membranes with Coomassie blue or Alcian blue as described in Example 4.

EXAMPLE 8

Tissue Fixation and Staining

Animals were anesthetized as described in Example 2 and the trachea, extrapulmonary bronchi, and lungs were removed and perfused intratracheally with a phosphate buffered 10% formalin solution (Fisher, Montreal, CAN) at 30 cm of fixative pressure for 24 hours as described by Tyler, W. S., et al. (1985). Fund. Appl. Toxic. 5:405–422]. After fixation, 3 consecutive transverse sections of the left lobe, including the main bronchus, was excised and embedded in paraffin. 4 μm sections were cut and stained with Alcian blue, pH 2.5/PAS, PAS, and Alcian blue; pH 2.5 and microscopically examined for histopathology.

EXAMPLE 9

Effect of Metabisulfite Exposure on Rat Airway Mucin Content

To determine if the assay is able to detect a change in airway mucin content in an animal model for hypersecretion, whole lung extracts from rats exposed to metabisulfite as described in Example 1 were Sepharose CL-6B chromatographed, blotted, deaminated and stained as described above. Rats exposed to metabisulfite weighed less than their $H_2O$ exposed counterparts (265.0±7.1 g and 351.5±3.2 g respectively). The weight of the lungs from metabisulfite treated animals had however increased from 0.44±0.03% body weight to 0.79 ±0.08% body weight. As shown in FIGS. 6A and 6B, metabisulfite caused a 7-fold increase in total PAS positive mucin and an approximate 3.5-fold increase in total Alcian blue staining mucin. Increases were also noted for the amount of PAS or Alcian blue reacting mucin per gram of wet tissue (4-fold and 2.3-fold respectively). These data are suggestive of both hypertrophic and hyperplastic changes for the mucus secreting epithelia of the rat airways following metabisulfite exposure. The increases in PAS and Alcian blue positive material is comprised entirely of HMW macromolecules as shown in FIG. 7A and 7B. Excluded material from control and metabisulfite treated animals was subjected to SDS electrophoresis on 2% agarose gels, transferred onto Immobilon-P membrane and stained, in order to test for the presence of HMW mucin. High molecular weight prestained protein standards (Bio-Rad) were not resolved and migrated with the dye front on the 2% agarose gel. Some Alcian blue staining was observed in lanes where control material was electrophoressed, however PAS positive material was not detected in the same samples. Samples prepared from metabisulfite treated lungs exhibited high levels of both PAS and Alcian blue HMW mucin material. No Alcian blue staining of mucin associated lower molecular weight proteins was noted (FIG. 3b). These results indicate that the increased PAS and Alcian blue staining observed in the fraction excluded from the Sepharose CL6B column is due entirely to HMW mucus glycoprotein present in the airway tissue and not due to lower molecular weight proteins.

Histological sections of the lung tissues were prepared to determine if the measured changes accurately reflected cellular changes in the airway. As shown in FIG. 8A and 8B, tissue from metabisulfite treated animals exhibited an increase in PAS/Alcian blue staining of the epithelial cell layer. The increase in staining results from more cells that contain mucus and as well, those cells which contain mucus appear more heavily loaded with the material when compared to control. The epithelial cells in metabisulfite treated airways also took on a columnar appearance versus the cuboidal morphology frequently seen in controls.

These changes are consistent with hypertrophic and hyperplastic alterations in the mucus secreting epithelia. A dramatic thickening of the basement membrane is also seen. Significant amounts of PAS/Alcian blue staining material were also present in the lumens of the main bronchi, bronchioles and in some alveolar spaces. Individual staining of sections with either PAS or Alcian blue both showed increases in the number of cells containing densely packed mucus containing granules following metabisulfite exposure.

EXAMPLE 10

Amounts of neutral and acidic mucus glycoproteins extracted from tracheae of control and MBS treated animals were measured as shown in FIG. 9a. Control rats exhibited 40-fold more Alcian blue staining than PAS staining mucus glycoproteins per gram trachea, 11.70±0.81 mg/g vs. 0.27±0.05 mg/g, respectively. Exposing animals to aerosolized $H_2O$ for a three week period results in a small non-significant increase in neutral mucus glycoprotein. Tracheal neutral mucus glycoproteins per gram trachea were elevated 4-fold in rats subjected to MBS compared to their $H_2O$ treated counterparts (FIG. 9b). No significant differences were measured for the acidic tracheal mucus glycoproteins.

EXAMPLE 11

Bronchial alveolar ravages were performed on rats which had been exposed to sodium metabisulfite mist for 2 and 3 weeks. As shown in FIG. 11, an approximate 10-fold increase in both Alcian blue and PAS positive mucus glycoprotein material was measured in lavage samples of sodium metabisulfite exposed animals compared to their respective controls. This data is consistent with the airway mucus plugs observed in histological sections prepared form metabisulfite exposed animals. It would appear that exposing rats to aerosolized sodium metabisulfite results in similar changes in the airway as those observed in persons afflicted with chronic obstructive pulmonary disease.

EXAMPLE 12

To examine the neurogenic components which might contribute to airway mucus cell metaplasia, a muscarinic antagonist (atropine) was administered to the rats 30 minutes prior to sodium metabisulfite mist exposure. As shown in FIG. 12, atropine given at a dose of 2 mg kg reduced both total acidic and neutral mucus glycoproteins in the lung tissue of the sodium metabisulfite exposed animals. These results suggest the involvement of a cholinergic muscarinic mediated pathway in metabisulfite mist induced mucus cell metaplasia and suggests that compounds which inhibit this neurogenic reaction could be identified using the assay described in this patent disclosure.

EXAMPLE 13

The effect of 6 weeks $SO_2$ exposure on rat airway mucus glycoprotein content was examined in order to compare with those chances observed with sodium metabisulfite exposure. As shown in FIGS. 13 and 14, significant increases in both PAS and Alcian blue positives were measured in lung tissue of $SO_2$ exposed animals. Trachea from rats exposed to $SO_2$ exhibited only a significant increase in PAS staining material. The data are highly consistent with those obtained from sodium metabisulfite treated animals and support the notion that aerosolized sodium metabisulfite is an equivalent substitute treatment for $SO_2$ gas with respect to metaplastic changes in mucus secreting airway cells.

EXAMPLE 14

SDS Polyacrylamide Gel Electrophoresis of Airway Extract Material Eluting in the Column Void Volume Lung extracts were prepared as described in Example 2. Samples (150 μl) obtained from the void volume of Sepharose CL-6B chromatographed airway extracts were incubated in a buffer containing 2% SDS with 10 mM mercaptoethanol at 100° C. for 4 min. Samples (70 μl) were loaded onto 4–12% Tris-glycine acrylamide gels and electrophoresed at 100 V for 2 h. Proteins were transferred onto Immobilon-P membranes and stained with either Coomassie blue or Alcian blue as described in Example 3. Coomassie blue staining of void volume material indicated that the material eluting in the void fraction of the column contains considerable levels of low molecular weight protein. This is probably due to ionic interaction of LMW protein with mucin. Alcian blue staining of the void volume material revealed that a majority of the stainable material is of HMW.

EXAMPLE 15
Densitometric Scan of Void Volume Material from Control and Sodium Metabisulfite Exposed Rats Subjected to 4–12% SDS PAGE as Previoously Described in Example 3

Samples (150 μl) obtained from the void volume of Sepharose CL-6B chromatographed airway extracts were incubated in a buffer containing 2% SDS with 10 mM mercaptoethanol at 100° C. for 4 min. Samples (70 μl) were loaded onto 4–12% Tris-glycine polyacrylamide gels and electrophoresed at 100 V for 2 hr. Proteins were transferred to Immobilon-p™ membranes using a Bio-Rad trans-blot apparatus in a Towbin buffer. Membranes were stained with Alcian blue to identify HMW mucus glycoproteins as described in Example 4. Densitometric scans of each sample lane were performed with a scanning laser densitometer at 633 nm. Results show that 50% of the total material staining with Alcian blue comprises LMW material. Exposing animals to MBS results in significant changes only in HMW Alcian blue staining material. Furthermore, 15,000 units/20,000 units (75%) per MBS treated rat lung protein is HMW. In addition, 6250 units/8100 units (77%) per gram MBS rat tissue is HMW.

EXAMPLE 16
Effect of SDS on Airway Extract Elution Profile

One ml aliquots of an extract prepared from a MBS exposed rat was incubated with 10 mM mercaptoethanol and varying amounts of SDS (0.1% to 2%) for 2 min at 68° C. The aliquots were then chromatographed on Sephacryl S-300 HR at a flow rate of 2 ml/min with the saline buffer described in Example 3. Protein eluting from the column was monitored at 280 nm with a Pharmacia UV-Monitor and chart recorder. Results show the amount of protein eluting in the void fraction decreases with increasing concentrations of SDS as judged by the peak height in the elution profile. Since mucus glycoproteins do not exhibit an absorbance at 280 nm, these results would indicate that non-mucin LMW proteins were not co-eluting with the HMW glycoproteins.

EXAMPLE 17
SDS Polyacrylamide Gel Electrophoresis of SDS-Treated Airway Extract Material Eluting in the Column Void Volume Void volume fractions from lung extracts treated with varying amounts of SDS (see Example 16). Samples (70 μl) were loaded onto 4–12% Tris-glycine acrylamide gels and electrophoresed at 100 V for 2 h. Proteins were transferred onto Immobilon-p™ membranes and stained with Coomassie blue. The data showed that the amount of LMW protein eluted in the void volume is reduced with progressive increases in SDS concentrations.

EXAMPLE 18
Agarose Gel Electrophoresis of SDS-Treated Airway Extract Material Eluting in the Column Void Volume Void volume fractions of SDS treated airway extract (see Example 16) were incubated in a buffer containing SDS and 10 mM mercaptoethanol at 100° C. for 4 min. Samples (70 μl) were loaded onto 2% agarose Tris-glycine gels and electrophoresed at 100 V for 2 h. Proteins were transferred onto Immobilon-p™ membranes and stained with PAS or Alcian blue as described in Example 3. Data showed that HMW mucus glycoprotein are not affected to any significant extent by SDS treatment.

EXAMPLE 19
Effect of SDS on Measured Differences of Airway Mucus Content in Air and $SO_2$ Exposed Animals Airway extracts were prepared from animals exposed to air or 250 ppm $SO_2$ for 5 hr/day, 5 days/wk. The soluble extracts from each animal were treated with either 0.1% or 2.0% SDS as described in Example 16 and chromatographed on Sephacryl S-300 HR. The material eluting in the void volume was stained for neutral and acidic mucoproteins with PAS and Alcian blue stains, respectively, as described in Example 4. Data showed that samples from animals exposed to $SO_2$ and treated with 2.0% SDS exhibited about 100% increases in mucin content (PAS and Alcian blue) compared to air exposed animals. Similar samples from $SO_2$ exposed animals treated with 0.1% SDS exhibited smaller changes in mucin content when compared to air exposed animals.

EXAMPLE 20
Validation of the Assay Method as a model for Bronchoconstriction Lung tissue from animals exposed to $SO_2$ (250 ppm, 5 hr/day, 5 d/wk for 5 weeks) were extracted and measured for mucous glycoprotein as described in Example 3. Pulmonary function tests were performed on a separate group of animals which had also been exposed to $SO_2$. The results indicated that the changes in measured mucus and pulmonary function that were induced in the airways of treated animals were similar to that observed in patients afflicted with chronic bronchitis.

What is claimed is:

1. A method for the rapid estimation of hyperplastic and hypertrophic changes in animal airways in which acidic and neutral mucoproteins are specifically measured, which comprises the steps of:

a) exposing a test animal to a suspected inducer of airway cell hypertrophy or hyperplasia;

b) removing the lungs of the test animal and homogenizing the lungs in an appropriately buffered hypotonic solution containing reducing agents and protease inhibitors to produce an extract containing particulate and soluble matter;

c) removing particulate matter present in the extract produced according to step (b) to produce a soluble extract, and size-fractionating the soluble extract to remove low-molecular weight soluble material to produce a fraction containing high molecular weight material greater than or equal in molecular weight to 250,000 daltons;

d) immobilizing the high molecular weight material by blotting the material on a membrane and deaminating the blotted material;

e) separately staining the immobilized material for acidic mucoproteins with Alcian Blue and Periodic Acid Schiff's reagent for neutral mucoproteins; and, f) quantitating the Periodic Acid Schiff's reagent and Alcian Blue specific staining by measuring the optical density of staining.

2. The method of claim 1 wherein the membrane in step (d) is a polyvinylidene fluoride membrane.

3. The method of claim 1 wherein the deaminating of step (d) prior to proceeding with the staining of step (e) comprises incubating the blotted material with $NaNO_2$ and acetic acid.

4. The method of claim 1 which further comprises rendering the membrane with blotted and stained high molecular weight material of step (e) translucent with paraffin liquid or transparent with a lower alkanol of $C_5$–$C_{12}$, and optionally, dipping the transparent membrane in paraffin liquid to retain transparency, prior to proceeding with the quantitating of step (f).

5. The method of claim 4 wherein the lower alkanol is selected from the group consisting of 1-heptanol, octanal and dodecanol.

6. The method of claim 4 wherein the lower alkanol is 1-heptanol.

7. The method of claim 1 wherein the inducer of airway cell hypertrophy or hyperplasia is sodium metabisulfite.

8. The method of claim 1 wherein step (b) further comprises contacting said homoginized lung supernatant to an appropriately buffered hypotonic solution containing SDS and heating said solution at about 68° C. for about 2 minutes.

9. A method for the rapid estimation of hyperplastic and hypertrophic changes in animal airways in which acidic and neutral mucoproteins are specifically measured, which comprises the steps of:
   a) exposing a test animal to a suspected inducer of airway cell hypertrophy or hyperplasia;
   b) removing the lungs of the test animal and homogenizing the lungs in an appropriately buffered hypotonic solution containing reducing agents and protease inhibitors and between 0.1% and 2% SDS to produce an extract containing particulate and soluble matter;
   c) heating said soluble extract at about 68° C. for about 2 minutes in the presence of between about 0.1% and 2% SDS;
   d) removing particulate matter present in the extract produced according to step (b) to produce a soluble extract, and size-fractionating the soluble extract to remove low-molecular weight soluble material to produce a fraction containing high molecular weight material greater than or equal in molecular weight to 250,000 daltons;
   e) immobilizing the high molecular weight material by blotting the material on a membrane and deaminating the blotted material with $NaNO_2$ and acetic acid;
   f) separately staining the immobilized material for acidic mucoproteins with Alcian Blue and Periodic Acid Schiff's reagent for neutral mucoproteins;
   g) rendering the membrane with blotted and stained high molecular weight material of step (f) translucent with paraffin liquid or transparent with a lower alkanol of $C_5$–$C_{12}$, and optionally, dipping the transparent membrane in parafrin liquid to retain transparency; and,
   h) quantitating the Periodic Acid Schiff's reagent and Alcian Blue specific staining by measuring the optical density of staining.

10. The method of claim 9 wherein the hypotonic solution contains about 2% SDS.

11. An in vitro method for the rapid estimation of hyperplastic and hypertrophic changes in animal airways in which acidic and neutral muroproteins are specifically measured, which comprises the steps of:
   i) homogenizing lung tissue which has been previously exposed to a suspected inducer of airway cell hypertrophy or hyperplasia, in an appropriately buffered hypotonic solution containing reducing agents and protease inhibitors to produce an extract containing particulate and soluble matter
   ii) removing particulate matter present in the extract produced according to step (i) to produce a soluble extract, and size-fractionating the soluble extract to remove low-molecular weight soluble material to produce a fraction containing high molecular weight material greater than or equal in molecular weight to 250,000 daltons;
   iii) immobilizing the high molecular weight material by blotting the material on a membrane and deaminating the blotted material;
   iv) separately staining the immobilized material for acidic mucoproteins with Alcian Blue and Periodic Acid Schiff's reagent for neutral mucoproteins; and
   v) quantitating the Periodic Acid Schiff's reagent and Alcian Blue specific staining by measuring the optical density of staining.

12. The method of claim 11 wherein the membrane in step (iii) is a polyvinylidene fluoride membrane.

13. The method of claim 11 wherein the deaminating of step (iii) prior to proceeding with the staining of step (iv) comprises incubating the blotted material with $NaNO_2$ and acetic acid.

14. The method of claim 11 which further comprises rendering the membrane with blotted and stained high molecular weight material of step (iv) translucent with paraffin liquid or transparent with a lower alkanol of $C_5$–$C_{12}$, and optionally, dipping the transparent membrane in paraffin liquid to retain transparency, prior to proceeding with the quantitating of step (v).

15. The method of claim 14 wherein the lower alkanol is selected from the group consisting of 1-heptanol, octanol and dodecanol.

16. The method of claim 14 wherein the lower alkanol is 1-heptanol.

17. The method of claim 11 wherein the inducer of airway cell hypertrophy or hyperplasia is sodium metabisulfite.

18. The method of claim 17 wherein the hypotonic solution contains about 2% SDS.

19. The method of claim 11 wherein step (ii) further comprises contacting said homogenized lung supernatant to an appropriately buffered hypotonic solution containing SDS and heating said solution at about 68° C. for about 2 minutes.

20. An in vitro method for the rapid estimation of hyperplastic and hypertrophic changes in animal airways in which acidic and neutral mucoproteins are specifically measured, which comprises the steps of:
   i) homogenizing the lung tissue which has previously been exposed to a suspected inducer of airway cell hypertrophy or hyperplasia, in an appropriately buffered hypotonic solution containing reducing agents, protease inhibitors and between 0.1% and 2% SDS to produce an extract containing particulate and soluble matter,
   ii) heating said soluble extract at about 68° C. for about 2 minutes in the presence of between about 0.1% and 2% SDS;
   iii) removing particulate matter present in the extract produced according to step (i) to produce a soluble extract and size-fractionating the soluble extract to remove low-molecular weight soluble material to produce a fraction containing high molecular weight material greater than or equal in molecular weight to 250,000 daltons;

iv) immobilizing the high molecular weight material by blotting the material on a membrane and deaminating the blotted material with $NaNO_2$ and acetic acid;

v) separately staining the immobilized material for acidic mucoproteins with Alcian Blue and Periodic Acid Schiff's reagent for neutral mucoproteins;

vi) rendering the membrane with blotted and stained high molecular weight material of step (v) translucent with paraffin liquid or transparent with a lower alkanol of C5–C–12, and optionally, dipping the transparent membrane in paraffin liquid to retain transparency; and, vii) quantitating the Periodic Acid Schiff's reagent and Alcian Blue specific staining by measuring the optical density of staining.

* * * * *